(12) United States Patent
Bruin et al.

(10) Patent No.: US 9,901,554 B2
(45) Date of Patent: Feb. 27, 2018

(54) BIODEGRADABLE COMPOSITIONS SUITABLE FOR CONTROLLED RELEASE

(75) Inventors: Peter Bruin, Groningen (NL); Audrey Petit, Groningen (NL); Mike De Leeuw, Groningen (NL); Martin Piest, Groningen (NL); Ronald Meijboom, Groningen (NL)

(73) Assignee: INGELL TECHNOLOGIES HOLDING B.V., Groningen (NL)

( * ) Notice: Subject to any disclaimer, the term of this patent is extended or adjusted under 35 U.S.C. 154(b) by 14 days.

(21) Appl. No.: 14/008,645

(22) PCT Filed: Apr. 2, 2012

(86) PCT No.: PCT/EP2012/055993
§ 371 (c)(1),
(2), (4) Date: Apr. 8, 2014

(87) PCT Pub. No.: WO2012/131104
PCT Pub. Date: Oct. 4, 2012

(65) Prior Publication Data
US 2014/0219923 A1    Aug. 7, 2014

(30) Foreign Application Priority Data
Mar. 31, 2011    (EP) ..................... 11002675

(51) Int. Cl.
| | | |
|---|---|---|
| A61K 31/167 | (2006.01) | |
| A61K 9/00 | (2006.01) | |
| A61K 9/06 | (2006.01) | |
| A61K 47/34 | (2017.01) | |
| A61K 49/04 | (2006.01) | |
| C08G 63/664 | (2006.01) | |
| C08G 63/682 | (2006.01) | |
| A61K 31/415 | (2006.01) | |
| A61K 31/573 | (2006.01) | |
| A61K 38/13 | (2006.01) | |
| A61K 38/38 | (2006.01) | |
| A61K 38/47 | (2006.01) | |
| A61K 39/395 | (2006.01) | |
| A61K 51/06 | (2006.01) | |
| A61K 47/30 | (2006.01) | |
| A61K 47/50 | (2017.01) | |

(52) U.S. Cl.
CPC .......... *A61K 31/167* (2013.01); *A61K 9/0024* (2013.01); *A61K 9/06* (2013.01); *A61K 31/415* (2013.01); *A61K 31/573* (2013.01); *A61K 38/13* (2013.01); *A61K 38/385* (2013.01); *A61K 38/47* (2013.01); *A61K 39/395* (2013.01); *A61K 47/34* (2013.01); *A61K 49/04* (2013.01); *A61K 49/0442* (2013.01); *A61K 49/0457* (2013.01); *C08G 63/664* (2013.01); *C08G 63/6822* (2013.01); *A61K 47/30* (2013.01); *A61K 47/50* (2017.08); *A61K 51/06* (2013.01); *A61K 51/065* (2013.01)

(58) Field of Classification Search
None
See application file for complete search history.

(56) References Cited

U.S. PATENT DOCUMENTS

| | | |
|---|---|---|
| 2005/0036946 A1 | 2/2005 | Pathak et al. |
| 2007/0014848 A1 | 1/2007 | Buchholz et al. |
| 2007/0224236 A1 | 9/2007 | Boden |
| 2007/0265356 A1 | 11/2007 | Kim et al. |

FOREIGN PATENT DOCUMENTS

| | | | |
|---|---|---|---|
| CN | 101862454 A | 10/2010 | |
| EP | 0558965 A2 | 9/1993 | |
| EP | 0778304 A2 | 6/1997 | |
| EP | 0 863 745 B1 | 5/2004 | |
| EP | 2343046 A2 | 7/2011 | |

(Continued)

OTHER PUBLICATIONS https://www.sigmaaldrich.com/content/dam/sigma-aldrich/ docs/Sigma/Product_Information_Sheet/2/m4287pis.pdf.*
Yu, L., et al., Mixing a Sol and a Precipitate of Block Copolymers with Different Block Ratios Leads to an Injectable Hydrogel, Biomacromolecules 2009, 10, pp. 1547-1553, XP-002586070.
Jo, S., et al, Reverse Thermal Gelation of Aliphatically Modified Biodegradable Triblock Copolymers, Macromol. Biosci., 2006, pp. 923-928.
Yu, L et al., A Subtle End-Group Effect on Macroscopic Physical Gelation of Triblock Copolymer Aqueous Solutions, Angew, Chem. Int. Ed. 2006, pp. 2232-2235, Wiley-VCH Verlag GmbH & Co., KCaA, Weinheim XP-002586068.

(Continued)

*Primary Examiner* — James W Rogers
(74) *Attorney, Agent, or Firm* — Hudak, Shunk & Farine Co., LPA

(57) ABSTRACT

A special class of drug-depot forming triblock copolymers which are very suitable for the loading, containment and releasing of sensitive drugs such as proteins from biodegradable, injectable drug depots. How to visualize these depots for various imaging related purposes is described. A composition comprising a tri-block copolymer according to formula 1 B-A-B (1), wherein A stands for a linear poly-(ethylene glycol) block and wherein B stands for wherein B stands for a poly(lactide-co-ε-caprolactone) block, wherein the hydroxyl end-groups of the tri-block copolymer are at least partially acylated with an optionally substituted acyl having 2 to 12 C-atoms, C-atoms of the substituents included; an active ingredient, preferably a pharmaceutically active ingredient and a solvent, wherein the block ratio of the tri-block copolymer, which ratio is defined as the ratio between the sum of the average molecular weight of the B-blocks and the sum of the average molecular weight of the A-block ranges from 1.4 to 3.5. This composition is suitable for controlled release of a pharmaceutically active ingredient.

16 Claims, 11 Drawing Sheets

(56) References Cited

FOREIGN PATENT DOCUMENTS

| WO | 00 18821 A1 | 4/2000 |
| WO | 00 38651 A1 | 7/2000 |
| WO | 01 82970 A1 | 11/2001 |

OTHER PUBLICATIONS

Yu, L. et al., Temperature-Induced Spontaneous Sol-Gel Transitions of Poly(D,L-latic acid-co-glycolic acid) . . . , Journal of Polymer Science: Part A: Polymer Chemistry, Nov. 11, 2006, pp. 1122-1133, vol. 45, No. 6, Wiley InterScience, XP-002586069.

G.M. Zentner et al., "Biodegradable block copolymers for delivery of proteins and water-insoluble drugs", Journal of Controlled Release 72 (2001) 203-215, published by Elsevier Science B.V. 2001; www.elsevier.com/locate/jconrel.

\* cited by examiner

BIODEGRADABLE COMPOSITIONS SUITABLE FOR CONTROLLED RELEASE

FIELD OF THE INVENTION

The invention relates to a composition comprising a tri-block copolymer, a solvent and a (pharmaceutically) active ingredient, said composition for use as a medicament, a process for the preparation of said composition and to a method for delivering a (pharmaceutically) ingredient over an extended period to an animal, including a human using said composition. Furthermore this composition can be combined with radiopaque atoms and molecules whereby the composition becomes visible under CT or other imaging techniques.

BACKGROUND OF THE INVENTION

In recent years, there has been considerable effort to provide systems that are capable of controlled release of drugs in animals, including humans. Some drugs can only be administered to a patient by injection. Controlled release of such drugs has the advantage that the patient does not need to be subjected to multiple injections, but instead only one or a few injections with the controlled release system would suffice.

Some injections into areas of the patient's body are (very) painful and intrinsically increase the risk of infection. Examples of such difficult to dose areas are the eyes, the (synovial) joints, the muscles or the spine. Injection with a drug in a controlled release system will limit the amount of injections needed and will enhance the chance that a patient will continue with the therapy and/or reduce the risk of infection. This will greatly increase the success of the treatment.

Controlled release systems that are very suitable for being injected into such difficult to dose areas are thermogels based on compositions comprising polymers. The polymers have the unique property that at low temperatures they are water soluble, whereas at higher temperatures the polymers become insoluble and form a gel. Preferably, for use as a system that is capable of controlled release, the polymer is soluble in the solvent used at room temperature (e.g. 21° C.) and forms a gel once injected into the body (temperature in the range from 30 to 42° C.).

A gel (or a hydrogel in the context of the present invention) is a network of polymer chains that are hydrophilic and contain a substantial amount of water (for example between 50 and 99% water, preferably between 66 and 85% water). The gel shows no flow in a vial tilt test: when a glass vial which contains the gel is turned upside down, no flow of the gel is observed during 15 seconds observation time.

Such thermogels are known from for example Zentner et al., Biodegradable block copolymers for delivery of proteins and water-insoluble drugs, Journal of Controlled Release 72 (2001), 203-215. In this article, the release of several drugs from BAB-type biodegradable thermal gels (marketed under the name ReGel®) is described. This ReGel® polymer is a water soluble, biodegradable polymer at temperatures below the gel transition temperature (so at the injection temperature) and forms a hydrogel inside the patient once injected. The hydrogel forms a controlled release drug depot and according to the article is capable of stabilizing poorly soluble and sensitive drugs, including proteins.

In this article, an example of a drug that is highly soluble in water is given: the in vitro release of g-CSF in 23% w/w ReGel® is described. However, as can be seen from FIG. 13, the drug is already released for 60% by the ReGel® system in the first two days. Such so-called burst release is not very advantageous for drugs which require a more constant dosage, such as peptides or anti-inflammatory drugs. For such drugs, a more linear release profile is desired and therefore, it is the object of the invention to provide compositions that are very suitable for controlled release of water soluble drugs (by forming a gel) with a decreased burst release, preferably with a linear release profile.

Within the framework of the invention, with 'water soluble compound' is meant that the solubility of the compound in water measured at 20° C. and at atmospheric pressure (1 bar) is at least 20 µg/ml. Solubility in water is determined using the method as described in the Pharmaceutical codex, twelfth edition, page 42, hereby included by reference. For example, the solubility may be determined by shaking an excess of the compound to be dissolved with water at 20° C. at atmospheric pressure (1 bar) until an equilibrium is reached. The solution is then filtered to remove the undissolved compound and the concentration of the dissolved compound is determined by liquid chromatography with UV-absorbance using a calibration curve of the dissolved compound.

SUMMARY OF THE INVENTION

This object is achieved by a composition comprising a tri-block copolymer according to formula 1

$$B\text{-}A\text{-}B \quad (1)$$

wherein A stands for a linear poly-(ethylene glycol) block and wherein B stands for wherein B stands for a poly(lactide-co-ε-caprolactone) block, wherein the hydroxyl end-groups of the tri-block copolymer are at least partially acylated with an optionally substituted acyl having 2 to 12 C-atoms, C-atoms of the substituents included; an active ingredient, preferably a pharmaceutically active ingredient and a solvent, wherein the block ratio of the tri-block copolymer, which ratio is defined as the ratio between the sum of the average molecular weight of the B-blocks and the sum of the average molecular weight of the A-block ranges from 1.4 to 3.5.

Preferably, in the composition of the present invention, the block ratio of the tri-block copolymer ranges from 1.4 to 2.6, the number average molecular weight (Mn) of the linear poly-(ethylene glycol) block is at least 1250 Da and the acyl is an optionally substituted acetyl, an optionally substituted propionyl, an optionally substituted butyl group, for example an optionally substituted n-butyl or i-butyl group; or an optionally substituted benzoyl group, for example an optionally substituted acetyl, an optionally substituted propionyl or an optionally substituted butyl group.

DETAILED DESCRIPTION OF THE INVENTION

The inventors have found that a composition according to the invention wherein the hydroxyl end-groups of the tri-block copolymer are at least partially covalently modified (as opposed to ReGel® polymers which have unmodified end-groups) and wherein the block ratio of the tri-block copolymer ranges from 1.4 to 3.5 is very suitable for controlled release of water soluble drugs. The composition according to the invention shows controlled release at a temperature of 30-42° C. (body temperature) for an extended time and hardly shows any burst release of the active ingredient. In many cases, the compositions according to the invention are also capable of a more or less linear release of the active ingredient, preferably both hydrophobic and water soluble drugs, more preferably water soluble drugs.

The terms 'pharmaceutically active ingredient' and 'drug' are used interchangeably herein.

That the composition according to the invention is capable of controlled release for an extended time release with hardly any burst release of the pharmaceutically active ingredient is surprising in view of US 2007/0265356 A1. US 2007/0265356 A1 discloses a thermogelling, aliphatically modified polymer for use in drug delivery. Illustrative embodiments of US 2007/0265356 A1 comprise a composition of matter comprising an aliphatically modified poly (L-lactide-co-ε-caprolactone)-poly-(ethylene glycol)-poly (L-lactide-co-ε-caprolactone), wherein the block ratio of the Mn of the B blocks and the Mn of the A block is 1.13, 1.28, or 1.25 respectively (see Table 1 of US 2007/0265356). US2007/0265356 teaches that phase separation in the body is favourable for drug delivery applications, since it causes spontaneous exclusion of water, thereby increasing the density of the polymeric gel and its stability and extending the drug release.

However, with the composition of the invention, phase separation in the body (temperature from 30 to 42° C.) does not occur whereas the composition does show controlled release for an extended time and hardly shows any burst release of the pharmaceutically active ingredient.

Besides a diminished burst release in the first hours or days, also the burst release of the composition of the invention immediately upon injection may be reduced.

Another advantage of the composition of the invention may be that the release of the active ingredient, preferably the pharmaceutically active ingredient may be prolonged. Yet another advantage of the composition of the invention may be its ability to stay intact under mild sheer or mild pressure forces inside the body.

Yet another advantage of the composition of the invention may be that due to the limited burst release, more drug may be loaded without running the risk of a toxic concentration at the site of injection upon the initial release of the drug.

In the tri-block copolymer according to formula (1)

A stands for a linear poly-(ethylene glycol) block (PEG block). Generally, the number average molecular weight (Mn) of the PEG block in the tri-block copolymer is at least 750 Da, for example at least 1000 Da, for example at least 1250 Da, 1500 Da and/or preferably at most 5000 Da, for example at most 2000 Da. For example, the average molecular weight of the PEG block ranges from 1000 to 5000 Da, preferably from 1000 to 2000 Da, for example from 1000 to 1500 Da. The number average molecular weight of the PEG block is the Mn given by the supplier. The rest of the number average molecular weights as used herein can then be calculated by comparing integrals of the peak of PEG and peaks of incorporated monomers using $^1$H NMR.

Poly-(ethylene glycol) is a diol also known as poly (ethylene oxide) and both names can be used interchangeably for the purpose of the invention.

B stands for a poly(lactide-co-ε-caprolactone) block (PLCA block), which PLCA block is a copolymer of lactide and ε-caprolactone. Within the framework of the invention the term lactide refers to all enantiomerically enriched, racemic forms and cyclic ester forms of lactic acid, such as L-lactide, D-lactide and DL-lactide.

The number average molecular weight of each individual PLCA block as determined using $^1$H NMR as described herein is generally at least 400 Da, for example at least 450 Da, preferably at least 500 Da and/or at most 1500 Da, for example at most 2000 Da, for example at most 2500 Da, preferably at most 3000 Da. For example, the number average molecular weight of the PLCA block ranges from 400 to 3000, for example from 450 to 2000, for example from 500 to 1500 Da.

The block ratio of the tri-block copolymer is defined as the ratio between the sum of the number average molecular weight (Mn) of the B-blocks and the number average molecular weight (Mn) of the A-block, wherein the number average molecular weight of the A-block and of the B-blocks is determined using the information from the supplier for the Mn of the PEG and $^1$H NMR as described above.

The block ratio may range from at most 3.5, for example at most 3.3, for example at most 3.0, for example at most 2.8, for example at most 2.6, for example at most 2.4 and/or for example at least 1.4, for example at least 1.6, for example at least 1.8, at least 1.9, for example at least 2.0.

Preferably, the block ratio ranges from, for example from 1.4 to 2.6, for example from 1.8 to 2.6, for example from 1.8 to 2.4.

The hydroxyl end-groups of the tri-block copolymer are at least partially acylated with an optionally substituted acyl having 2 to 12 C-atoms, C-atoms of the substituents included. The acyl group may be represented by a compound of formula (2)

$$R^1\text{—C(O)—} \qquad (2)$$

wherein $R^1$ stands for an optionally substituted alkyl, optionally substituted alkenyl, optionally substituted alkynyl or optionally substituted aryl, preferably for an optionally substituted alkyl or optionally substituted aryl, preferably an optionally substituted alkyl and wherein the $R^1$—C(O) group is covalently linked to the tri-block copolymer.

Examples of $R^1$ include but are not limited to linear and branched alkyls, for example methyl, ethyl, n-propyl, i-propyl, n-butyl, i-butyl, pentyl, hexyl, heptyl, octyl, nonyl, decyl and undecyl; linear and branched alkenyls; and linear and branched alkynyls. $R^1$ may also stand for the cyclic form of the alkyl, alkenyl or alkynyl. An example of optionally substituted aryl includes but is not limited to phenyl and halogen, for example iodine substituted phenyls.

Preferably, $R^1$ stands for an alkyl, preferably for methyl respectively ethyl. (in other words the acyl group is acetyl respectively propionyl).

$R^1$ may optionally be substituted with a functionalized group, for example with a group containing a heteroatom, for example O, N, for example an $NH_2$ group, S, for example an SH group, halogen, for example a fluoride, chloride or iodine group, preferably with iodine.

In a special embodiment of the invention, the acyl group may be substituted with a radiopaque atom, for example iodine. For example, an acyl group substituted with a radiopaque atom may be iodobenzoyl.

The radiopaque atoms may be visualized in situ using X-ray, for example 2D or 3D CT (X-ray computed tomography).

The invention therefore also relates to a composition comprising a tri-block copolymer according to formula (1)

wherein A stands for a linear poly-(ethylene glycol) block and wherein B stands for wherein B stands for a poly (lactide-co-ε-caprolactone) block,
wherein at least part of the hydroxyl end-groups of the tri-block copolymer are covalently bound to a compound containing radiopaque atoms.

Preferably, the radiopaque atom is iodine.

Preferably, said composition further comprises an active ingredient, preferably a pharmaceutically active ingredient and/or a solvent.

By including a pharmaceutically active ingredient in said composition, it is possible to correlate the degree of gel erosion with the degree of release of pharmaceutically active ingredient from the gel.

Preferably, the block ratio of the tri-block copolymer in said composition, which ratio is defined as the ratio between the sum of the number average molecular weight of the B-blocks and the number average molecular weight of the A-block ranges from 1.4 to 2.6.

By covalently binding the hydroxyl end-groups of the tri-block copolymer to a compound containing radiopaque atoms, many applications of said compositions become available:

For example, it may be visualized where a composition of the invention has been injected. This 3D in situ marking of a location may be useful, for example in radiotherapy for example breast or prostate cancer, where it is necessary to focus the energy beam at exactly the same location for sequential radiation exposures.

Current positioning techniques include surgical introduction of small objects of gold, titanium or other electron dense objects that give sufficient contrast in x-ray and CT-imaging. However, these 'contrast agent markers or beckons are permanent and as such less attractive for the patient and may eventually cause scare tissue and bio-mechanic complications.

Also, in situ marking of a location may be useful when during surgery an area is marked, which needs a follow-up. For example, during endoscopic inspection of the colon and other externally accessible parts of the body, small surgical procedures may be performed either on the spot, or during a follow-up session, to burn or cut away tissue, such as small neoplasmas in the colon, which potentially could develop into tumours in the colon. Leaving behind a radiopaque gel depot will greatly facilitate revisiting of the site for inspection for follow-up procedures, thereby using image-guided techniques for positioning.

Treatment and subsequent inspection and follow-up of lesions in the gut, stomach or lung are done at shorter intervals, but again, the in situ marking of a location is desired.

Currently, to actually pin-point and revisit or inspect a previous site of treatment is not easy, as the form, shape and position, for example of the colon, may fold and twist and may alter the external positioning parameters.

Also, the temporary in situ marking of a location in vivo may be useful when successive injections need to be made at or next to previous injection sites. These radiopaque gels are far more compatible to the surrounding tissue than metal objects, and if desired, will erode away over time.

Furthermore, in the composition of the invention, the radiopaque atom stays with the gel since the atom forms part of the tri-block copolymer. This in contrast to other contrasting agents, which will readily diffuse away from the injection site.

As indicated before, the residence time of the composition of the invention can be anything in the range from some days to months.

Preferably, in said compositions, chemical hydrolysis or enzymatic cleavage at physiological conditions in situ of the tri-block copolymer wherein at least part of the hydroxyl end-groups of the tri-block copolymer is covalently bound to a compound containing one or more radiopaque atoms is limited, for example by choosing a suitable end-group linker and/or a suitable monomer, for example a hydrophobic monomer to link the compound containing one or more radiopaque atoms to.

Also, the composition of the invention comprising the tri-block copolymer wherein at least part of the hydroxyl end-groups of the tri-block copolymer is covalently bound to a compound containing one or more radiopaque atoms could be used to observe gel-erosion in vivo and to be able to correlate the gel-volume with degree of release of pharmaceutically active ingredient.

The tri-block copolymer wherein at least part of the hydroxyl end-groups of the tri-block copolymer is covalently bound to a compound containing one or more radiopaque atoms may be blended with a tri-block copolymer that does not contain a compound containing one or more radiopaque atoms to fine tune for example i) the quantity, ii) the contrast intensity and iii) the duration of retention on the spot of injection. Modification of the hydroxyl end-groups of the tri-block copolymers in the composition of the invention also offers the possibility to introduce multifunctionality. For example, the hydroxyl group of the tri-block copolymer may be modified with heteroatoms which might increase the affinity of the drug for the micelle (hydrogen bonds) or unsaturation (pi-pi interaction) and/or which are imageable, such as iodo groups, which can be imaged by X-ray or MRI, or may be modified with a compound that interacts with (and could also stabilize) the active ingredient or may be modified with cell-attracting moieties, such as the cell adhesive RGD peptide. The latter may provide a method for recruiting cells into/onto the thermogel after injection into the body.

In another aspect therefore, the invention relates to a method for imaging a position within the body of a warm-blooded species comprising the steps of:
injecting a composition comprising a tri-block copolymer accordingly to formula (1)

$$B\text{-}A\text{-}B \quad (1)$$

wherein A stands for a linear poly-(ethylene glycol) block and wherein B stands for a poly(lactide-co-ε-caprolactone) block, wherein at least part of the hydroxyl end-groups of the tri-block copolymer are covalently bound to a compound containing a radiopaque atom of the invention into the body of the warm-blooded species and imaging the composition using conventional imaging methods such as CT or micro CT.

The hydroxyl end-groups of the tri-block copolymer may be acylated using methods known in the art, for example by reaction of the hydroxyl end-groups with an acid chloride or with an anhydride. For example, acylation of the hydroxyl end-groups of the tri-block copolymer may be done using acetyl chloride (which is an unsubstituted acyl having 2 C-atoms), with propionyl chloride (which is an unsubstituted acyl having 3 C-atoms), etc.

For example, acylation of the hydroxyl end-groups of the tri-block copolymer may be done by reacting with the corresponding anhydride in pyridine at elevated temperature.

With 'at least partially acylated' is meant that the percentage of hydroxyl end-groups that can be acylated (also referred to as the 'degree of modification' or the 'degree of acylation') is higher than 0 and at most 100%; for example the degree of modification of the hydroxyl end-groups is at least 10%, for example at least 25%, for example at least 30%, for example at least 35%, for example at least 40%, for example at least 75% and/or at most 95%, for example at most 90%, preferably 100%.

For the avoidance of doubt, a degree of modification of 100% means that all hydroxyl end-groups of the tri-block copolymer have been modified; a degree of modification of 50% means that half of the hydroxyl end-groups have been modified. The degree of modification, is preferably calculated using $^1$H nuclear magnetic resonance by comparing integrals of the peaks due to the acylated hydroxyl end-groups and the integrals of the polyethylene glycol (as a measured for the amount of non-acylated hydroxyl end-groups).

The synthesis of the tri-block copolymer as used in the composition of the invention can be done using methods known in the art, for example by ring-opening polymerization or polycondensation reactions. For example, the tri-block copolymer may be synthesized (analogous to) the method described by Seongbong, Jo et al. in 'Reverse thermal gelation of aliphatically modified biodegradable tri-block copolymers', Macromol. Biosci. (2006), pages 923-928, which article is hereby included by reference. FIG. 1 as described herein gives the reaction scheme for the synthesis of a tri-block copolymer of PLCA-PEG-PLCA and its acylation of the hydroxyl end-groups with aliphatic acid chloride.

B blocks can be polymerized by using the cyclic monomers mentioned above in a ring-opening polymerization using the hydroxyl end-groups of poly(ethylene glycol) to initiate the polymerization. This is a very controlled and straightforward way of preparing tri-blocks in one step for people skilled in the art. Schemes and details for similar ring-opening polymerization reactions can be found in several patents or patent applications including and not limited to EP0863745 and WO0018821.

Preparing B blocks by polycondensation reactions using the open form of the cyclic monomers mentioned above, such as lactic acid, glycolic acid, epsilon-hydroxyhexanoic acid and the like is also possible, but less preferred since obtaining well-defined blocks in terms of average molecular weight and end-group functionality with polycondensation reactions is difficult.

Acylation of the hydroxyl end-groups may be done using methods known in the art, for example (analogous to) the method described in Seongbong, Jo et al. in 'Reverse thermal gelation of aliphatically modified biodegradable tri-block copolymers', Macromol. Biosci. (2006), pages 923-928, and as illustrated by FIG. 1 therein, which article is hereby included by reference.

The number average molecular weight (Mn) of the tri-block copolymer depends on the number average molecular weight of the PCLA and PEG blocks used. The number average molecular weight of the tri-block copolymer may be calculated using $^1$H nuclear magnetic resonance. Preferably the Mn of the tri-block copolymer ranges from 3,000 to 5,000 Da.

The active ingredient in the composition of the present invention may be an active ingredient such as any pharmaceutically active ingredient and any diagnostic and any contrast agent and includes those pharmaceutically active ingredients having a prophylactic effect on the animal, including human as well as those pharmaceutically active ingredients that have an effect of alleviating, reducing or even completely eliminating a symptom, or a cause, or a consequence of a disease, such as pain, swelling or inflammation or a disease from the animal, including human.

For example, the pharmaceutically active ingredient may include broad classes of compounds normally delivered into the body. For example, these pharmaceutically active ingredients include but are not limited to anti-infectives (including antibiotics, antivirals, fungicides, scabicides or pediculicides); antiseptics (e.g. benzalkonium chloride, benzethonium chloride, chorhexidine gluconate, mafenide acetate, methylbenzethonium chloride, nitrofurazone, nitromersol and the like); analgesics and analgesic combinations; anorexics; antihelminthics, antiarthritics, antiasthmatic agents; anticonvulsants; antidepressants; antidiabetic agents; antidiarrheals; antihistamines; anti-inflammatory agents, antimigraine preparations; antinauseants; antineoplastics; antiparkinsonism drugs; antipuritics; antipsychotics; antipyretics, antispasmodics; anticholinergics; sympathomimetics; xanthine derivatives; cardiovascular preparations including potassium and calcium channel blockers; beta-blockers; alpha-blockers and antiarrhythmics; antihypertensives; diuretics and antidiuretics; vasodilators including general coronary, peripheral and cerebral vasodilators; central nervous system stimulants; vasoconstrictors; cough and cold preparations, including decongestants; hormones and steroids (e.g. estrogens, progestins, androgens, adrenocorticoids, corticosteroids and the like); hypnotics; immunosuppressives; muscle relaxants; parasympatholytics; psychostimulants; sedatives and tranquilizers, narcotics (e.g. morphine, meperidine, codeine and the like), local anesthetics (e.g. amide- or anilide-type local anesthetics such as bupivacaine, dibucaine, mepivacaine, procaine, lidocaine, tetracaine and the like); antiemetic agents (e.g. ondansetron, granisetron, tropisetron, metoclopramide, domperidone, scopolamide and the like); antiangiogenic agents (e.g. combrestatine, contortrostatin, anti-VEGF and the like), polysaccharides, immune-modulating, anti-thrombogenic compounds, anti-claudicating drugs, anti-atherosclerotic drugs, antihistamines, anti-cancer drugs (e.g. mechlorethamine, cyclophosphamide, fluorouracil, thioguanine, carmustine, lomustine, melphalan, chloambucil, streptozocin, methotrexate, vincristine, bleomycin, vinblastine, vindesine, dactinomycine, daunorubicin, doxorubicin, tamoxifen, paclitaxel, epirubicin, mitomicin C, cisplatin, carboplatin, and the like and photosensitizers used in photodynamic therapy, vascular drugs, ophthalmic drugs, amino acids, vitamins, neurotransmitters, neurohormones, signaling molecules, psychoactive medicaments, synthetic drugs, semi-synthetic drugs, natural drugs and substances derived from these, or combinations of the above.

The pharmaceutically active ingredient may also be a biological including but not limited to (recombinant) proteins, PEGylated-proteins and peptides (e.g. insulin, erythropoietin, exenatide, glucagon-like-peptide-1, morphogenic proteins (e.g. bone morphogenic proteins, transforming growth factors, fibroblast growth factors, tumor necrosis factors), receptor antagonists (e.g. Interleukin-1-receptor-antagonist), anticancer proteins (e.g. neocarzinostatin, L-asparaginase, interleukin-2, bevacizumab and other anti-VEGF agents) prophylactic vaccines, therapeutic vaccines, genetic materials (e.g. nucleic acid sequences, polynucleotides, (antisense) oligonucleotides, plasmids, DNA, RNA, siRNA, microRNA), aptamers, enzymes, antigens, antibodies, antibody fragments, viruses, virus-based materials, cells, cellular substructures, etc.), Prodrugs, metabolites, derivatives, in-vivo or in in-vitro chemically modified products, in-vivo or in-vitro enzymatic modified products and pharmaceutically active degradation products of the pharmaceutical active ingredients described herein are included in the scope of the invention.

Preferably, the active ingredient is a pharmaceutically active ingredient chosen from the group of immune-modifying drugs, anti-inflammatory drugs or growth factors.

Preferably, the active ingredient is a pharmaceutically active ingredient chosen from the group of immune-modifying drugs for example cyclosporine, tacrolimus (FK-506), sirolimus or rapamycin.

Preferably, the active ingredient is a pharmaceutically active ingredient chosen from the group of steroidal anti-inflammatory drugs, for example prednisone, prednisolon, triamcinolon, clobetasol or betamethason.

Preferably, the active ingredient is a pharmaceutically active ingredient chosen from the group of non-steroidal anti-inflammatory drugs, for example aspirin, diclofenac, piroxicam, meloxicam, ibuprofen or a selective COX-2 inhibitor for example celecoxib, valdecoxib, etoricoxib or rofecoxib.

Preferably, the active ingredient is a pharmaceutically active ingredient chosen from the group of anticancer agents for example bevacizumab, tamoxifen or interleukin-2.

Preferably, the active ingredient is a pharmaceutically active ingredient chosen from the group of anti-viral agents for example acyclovir or oseltamivir.

Preferably, the active ingredient is a pharmaceutically active ingredient chosen from the group of anti-bacterial agents for example amoxicillin.

Preferably, the active ingredient is a pharmaceutically active ingredient chosen from the group of anti-diabetic agents for example insulin, glucagon-like-peptide-1, exenatide.

Preferably, the active ingredient is a pharmaceutically active ingredient chosen from the group of vaccines.

Preferably, the active ingredient is a pharmaceutically active ingredient chosen from the group of ophthalmic agents for example Triamcinolone and Bevacizumab.

Preferably, the active ingredient is a pharmaceutically active ingredient effective against forms of neuro-degenerative diseases such as apomorphine, rivastigmine, pramipexole, pioglitazone, memantine and safinamide.

Preferably, the active ingredient is a pharmaceutically active ingredient chosen from the group of biologicals including but not limited to growth factors which are very suitable for application in orthopedics and in particular in the prevention or treatment of diseases of intervertebral discs, or cartilage, or bone. Examples of such growth factors include but are not limited to transforming growth factor 3, fibroblast growth factor 18, osteogenic protein 1, bone morphogenic protein 2, bone morphogenic protein 6, bone morphogenic protein 7, interleukin-1-receptor-antagonist.

Preferably, the active ingredient belongs to the class of human growth hormones and its biosimilar derivatives, which can be applied in both pediatric and adult growth disorders, maintenance of sufficient musculature, and for anti-ageing applications.

Preferably, the active ingredient is a pharmaceutically active ingredient effective against inflammation or microbial infections of the inner ear and its connecting tissues, (intratympanic ear diseases).

Preferably, the active ingredient is a pharmaceutically active ingredient effective against forms of diabetes, for example glucagon-like-peptide-1, and its derivatives such as exendin-4 and liraglutide.

For the active ingredient which are water soluble, the drug preferably has a solubility in water of at least 20, for example of at least 100, for example of at least 500 µg/ml, for example of at least 1000 µg/ml, for example of at least 5000 µg/ml in water measured at 20° C. and at atmospheric pressure (1 bar).

Examples of water soluble active ingredients include small molecules (of up to 5,000 Da), medium sized molecules (of up to 10,000 Da), but also large molecules (of at least 10,000 Da), such as proteins. These water soluble active ingredients may be synthesized chemically, but may also be a biological including but not limited to (recombinant) proteins and peptides (e.g. insulin, erythropoietin, exenatide, glucagon-like-peptide-1, morphogenic proteins (e.g. bone morphogenic proteins, transforming growth factors, fibroblast growth factors, tumor necrosis factors), receptor antagonists (e.g. Interleukin-1-receptor-antagonist), anticancer proteins (e.g. neocarzinostatin, L-asparaginase, interleukin-2, bevacizumab and other anti-VEGF agents) prophylactic vaccines, therapeutic vaccines, genetic materials (e.g. nucleic acid sequences, polynucleotides, (antisense) oligonucleotides, plasmids, DNA, RNA, siRNA, microRNA), aptamers, enzymes, antigens, antibodies, antibody fragments, viruses, virus-based materials, cells, cellular substructures, etc.).

Therefore, the invention also relates to a composition according to the invention, wherein the active ingredient is a pharmaceutically active ingredient selected from the group of water soluble drugs, that is drugs that have a solubility in water of at least 20 µg/ml as determined using the method described herein.

The invention also relates to a composition, wherein the composition further comprises nano-particles and/or microparticles (such as liposomes and microspheres) which particles contain any of the Pharmaceutically active ingredients as described above.

The solvent in the composition of the present invention is preferably a solvent that is non toxic, preferably also biocompatible, and approved by regulatory instances, preferably aqueous based or a so-called FDA (Federal Drug Administration) class 3 solvent.

Examples of solvents include but are not limited to water, mixtures of water and an organic solvent like for example ethanol, isopropanol or dimethylsulfoxide (DMSO); aqueous buffer solutions, preferably aqueous buffer solutions that lead to isotonic compositions of the invention, such as PBS (phosphate buffered saline) or Sorenson modified buffer or variants thereof; and organic solvents, such as ethylacetate, acetone, dichloromethane (DCM), dimethylsulfoxide (DMSO), N-methylpyrrolidone (NMP), isopropyl myristate and benzyl benzoate.

The compositions as described in this patent application are of use in all diseases as classified by the World Health Organization, Document ICD-10 (2007) and where the dosing of pharmaceutical active agents as described above is common clinical or experimental practise in all animals including humans.

With 'isotonic' is meant that the solution a solution having an osmotic pressure comparable to or at least compatible with the osmotic pressure of human or animal body fluids, preferably with blood.

Preferably the solvent is water or an aqueous buffer solution, more preferably an aqueous buffer solution that leads to an isotonic composition of the invention.

The pH of the solvent is preferably in the range from 5 to 8, for example in the range from 6.5 to 7.5. More preferably, the pH of the solvent is chosen such that the pH of the composition of the invention is about neutral (in the range from 5 to 8, preferably in the range from 6.5 to 7.5).

With gel temperature is meant the temperature at which the tri-block copolymer in the solvent chosen forms a gel. Vial tilting as described below can be used to determine the gel temperature.

The gel temperature of the composition of the invention is preferably at least 20° C., more preferably at least 25° C., for example at least 30° C. and/or preferably at most 36, for example at most 35, for example at most 34° C. For example, the gel temperature of the composition of the invention ranges from 30 to 35° C.

With phase separation temperature is meant the temperature at which the different components present are not capable of forming a homogeneous solution, but instead form separate (liquid) phases. Phase separation can be determined using vial tilting. To this end, the compositions of the invention are vortexed and stored at 5° C. If needed, the samples were subjected to another heating and cooling cycle until all components in the composition of the invention were completely dissolved. The samples were evaluated by vial tilting at 5° C., then allowed to equilibrate at 20° C. for 30 minutes after which they were evaluated again. Visual observations were made and noted down. Next, the samples were placed in a water bath and slowly heated (less than 0.5° C./min). At every 1° C. increment, samples were evaluated by vial tilting and considered a gel if no flow was observed during a period of 15 seconds. Samples were heated until phase separation was observed and the temperature at which phase separation was observed is the 'phase separation temperature'.

Preferably, the phase separation temperature of the composition of the invention is at least 40° C., for example at least 41° C., for example at least 42° C.

Preferably, the composition of the invention has a gel temperature in the range from 25 to 25° C., for example from 30 to 35° C. and a phase separation temperature of at least 42° C.

Preferably, for clinical applicability, the tri-block copolymer has a gel window between 25 and 50° C., for example between 30° C. and 50° C., for example between 30° C. and 42° C. With 'gel window' is meant the 'window between the gel temperature and the phase separation temperature', in other words it is the entire temperature range in which the tri-block copolymer is a gel.

The concentration of the tri-block copolymer in the composition is for example at least 15% w/w, for example at least 17% w/w, for example at least 19% w/w, for example at least 20% w/w, for example at least 21% w/w, preferably at least 22% w/w, preferably at least 23% w/w, preferably at least 24% w/w, preferably at least 25% w/w based on the amount of solvent and active ingredient present in the composition, more preferably at least 27% w/w, even more preferably at least 30% w/w, for example at least 31% w/w, for example at least 32% w/w, for example at least 33% w/w, for example at least 34% w/w, for example at least 35% w/w, for example at least 36% w/w and/or preferably at most 50% w/w, for example at most 45% w/w, for example at most 44% w/w, for example at most 43% w/w, for example at most 42% w/w, for example at most 41% w/w, for example at most 40% w/w, for example at most 39% w/w based on the amount of solvent and active ingredient present in the composition.

For example, the concentration of the tri-block copolymer in the composition of the invention may range from 15 to 40% w/w, for example from 25 to 35% w/w based on the amount of solvent and active ingredient present in the composition.

If a higher concentration of tri-block copolymer is used, it may be that the composition can be loaded with higher amounts of (hydrophobic) drugs as compared to the loading capacity of the same tri-block copolymer at a lower concentration. This would especially be beneficial for patients having a chronic disease as it would allow to decrease the number of injections a patient requires even further. Also, or furthermore, a higher loading capacity may mean that the volume to be injected can be decreased. This would for example be beneficial for injections into areas where space is limited, for example for injections into joints or into ocular, intra-cranial cavities or intervertebral discs.

The tri-block copolymer in the composition of the invention may be varied on many parameters. Examples of variations that are possible in the tri-block copolymer include but are not limited to the Mn of the tri-block copolymer, Mn of the PCLA block, Mn of the PEG block, the choice of alkyl with which the hydroxyl end-groups of the tri-block copolymer may be covalently modified, the degree of modification of the hydroxyl end-groups of the tri-block copolymer, the block ratio and the weight ratio of ε-caprolactone and lactide in the PCLA block.

The weight ratio of ε-caprolactone to lactide is the weight of ε-caprolactone divided by the weight of lactide used to prepare the B-block with, in case the B-block is PLCA.

The weight ratio of ε-caprolactone to lactide is for example from 1/9 to 9/1, for example from 1/4 to 4/1. Preferably the weight ratio of ε-caprolactone to lactide is at least 1/1, for example from 1/1 to 1/0, for example from 1/1 to 9/1.

For the avoidance of doubt, with weight ratio of ε-caprolactone to lactide is 1/0 is meant that only|only ε-caprolactone is present and no lactide. With weight ratio of ε-caprolactone to lactide is 0/1 is meant that only lactide is present and no ε-caprolactone.

In a special embodiment, the invention relates to a composition of the invention, wherein the block ratio of the tri-block copolymer, which block ratio is defined as the ratio between the sum of the number average molecular weight of the B-blocks and the sum of the number average molecular weight of the A-blocks ranges from 1.8 to 2.4, wherein the ratio of ε-caprolactone/lactide in the tri-block copolymer ranges from 1/1 to 1/0 and wherein at least 10%, preferably at least 25% and most preferably at least 50% of the hydroxyl end-groups of the tri-block copolymer is modified.

The amount of active ingredient in the composition of the present invention depends on the amount to be administered to the animal, including human and on the duration of the release. For example, the amount of active ingredient may be up to and including 50% w/w based on the tri-block copolymer if a high loading of the drug is desired, but may also for example be less, for example an amount of up to and including 40, for example up to and including 30, for example up to and including 20% w/w based on the tri-block copolymer and/or for example at least 0.01% w/w, preferably at least 0.1 w/w, for example at least 1'% w/w based on the tri-block copolymer.

The invention also relates to a composition of the invention, wherein the composition is a pharmaceutical composition further comprising a pharmaceutically acceptable adjuvant, carrier or excipient.

A person skilled in the art knows which carriers can be used as pharmaceutically acceptable carriers. Examples of such pharmaceutically acceptable carriers are both inorganic and organic carrier materials, suitable for oral/parenteral/injectable administration and include water, polyethyleneglycol (PEG), polypropyleneglycol (PPG), cellulose derivatives, such as hydroxypropylmethylcellulose (HPMC), hydroxyethylmethylcellulose (HEMC), hydroxyethylcellulose (HEC); polyvinylpyrrolidone (PVP), polyvinylalcohol (PVA), gelatin, gum arabic, lactose, starch, magnesium stearate, talc, vegetable oils, and the like.

Also, the person skilled in the art knows which pharmaceutically acceptable adjuvants and excipients may be used in the compositions of the invention. Examples of conventional pharmaceutical additives and adjuvants, excipients or diluents, including, but not limited to, water, gelatin of any origin, polyethyleneglycol (PEG), polypropyleneglycol (PPG); cellulose derivatives, such as hydroxypropylmethylcellulose (HPMC), hydroxyethylmethylcellulose (HEMC) or hydroxyethylcellulose (HEC); polyvinylpyrrolidone (PVP), polyvinylalcohol (PVA), vegetable gums, ligninsulfonate, talc, sugars, starch, gum Arabic, vegetable oils, polyalkylene glycols, flavoring agents, preservatives, stabilizers, emulsifying agents, buffers, lubricants, colorants, wetting agents, fillers, imaging agents, such as contrast agents for X-ray or MRI; and the like, for exampleiodo compounds, such as the commercially available Xenetic® and Hexabrix®.

In another aspect, the invention relates to a composition according to the invention for use as a medicament.

In another aspect, the invention relates to a composition according to the invention for use as a medicament that is injected through a needle of at least 14 G, for example at least 18 G, for example at least 21 G, preferably at least 23 G, for example at least 27 G, for example at least 31 G.

With G is meant 'Gauge' which is a measure for the outer diameter of a needle. Smaller gauge numbers indicate larger outer diameters and as such 'larger needles'. For ease of injection, smaller needles are preferred to larger needles. Inner diameters of a needle depend on both gauge and wall thickness.

Depending on the pharmaceutically active ingredient or combination of pharmaceutically ingredients present in the composition of the invention, different diseases may be targeted, preferably treated using the composition(s) of the present invention.

In yet another aspect, the invention relates to a process for the preparation of a composition of the invention comprising the steps of synthesizing the tri-block copolymer and mixing the tri-block copolymer with the active ingredient and the solvent.

The order in which the tri-block copolymer and the active ingredient are dissolved in the solvent is in principle not critical; it is for example possible to first dissolve the tri-block copolymer and then the active ingredient, to first dissolve the active ingredient and then the tri-block copolymer or for example to dissolve both the active ingredient and the tri-block copolymer at the same time in the solvent of choice.

However, for active ingredients that are highly soluble in the solvent, preferably first the active ingredient is dissolved in the solvent to form a solution of the active ingredient in the solvent, after which the tri-block copolymer is dissolved into said solution or the polymer is dissolved at a higher concentration, when polymer dissolved a concentrated drug solution in the buffer of choice is added to get to the right polymer and drug concentration. For active ingredients that are less soluble in the solvent of choice, the active ingredient may first be dissolved into a solvent in which it is better soluble (for example a hydrophobic drug may be soluble in ethylacetate) together with the polymer, after which the solvent is evaporated and the solvent of choice is added to the (dried) polymer/drug mixture. This will increase the solubility of the active ingredient in the solvent of choice.

The invention can also contain and release micro- or nano-sized particles such as microspheres and liposomes which already contain for instance drugs, nucleotide sequences or imaging agents.

The benefit of combining the invention with these micro- or nano-sized particles is that the invention will ensure localization and gradual release of these particles, instead of a typical migration of such particles from the place of injection.

To facilitate dissolving the tri-block copolymer and/or the active ingredient the composition comprising the tri-block copolymer, the solvent and the active ingredient may be heated for example until the tri-block polymer melts. For example, the heating of the composition may be performed at 50° C.

Preferably, if the active ingredient is sensitive to heat, the tri-block copolymer may be melted (for example at a temperature of about 50° C.), dissolved into the solvent of choice after which the obtained solution may be cooled down and the active ingredient may be dissolved in the solvent.

In another aspect, the invention relates to a method for delivering an pharmaceutically active ingredient over an extended period, for example over a period of more than 1 day up to several, e.g. 6, months, to an animal, including a human requiring such treatment which comprises administering to such animal an effective amount of the composition of the invention.

In yet another aspect, the invention relates to a method for delivering an pharmaceutically active ingredient over an extended period, for example over a period of more than 1 day up to several, e.g. 6, months, to an animal, including a human requiring such treatment which comprises administering to such animal an effective amount of the composition of the invention through a needle of at least 14 G, for example at least 18 G, for example at least 21 G preferably at least 23 G, for example at least 27 G, for example at least 31 G.

In the framework of the invention, with animals is meant all animals, including mammals, examples of which include humans. Preferred examples of mammals beside humans include but are not limited to dogs, cats, dromedaris, camels, elephants, goats, mice, guinea pigs, rabbits, pigs, cows, water buffalos, kangaroos, monkeys and horses.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention is now elucidated by way of the following examples, without however being limited thereto.

EXAMPLES

Measurement Methods

The tri-block copolymer composition (PLCA/PEG ratio, cap/lac ratio and DM) was determined with proton nuclear magnetic resonance ($^1$H NMR; Varian, 400 MHz), using deuterated chloroform as solvent and reference. From the integration of various proton signals (due to PEG and incorporated monomers), absolute number average molecular weights $M_n$ were obtained. Mn of the tri-block copolymer is the sum of the molecular weights of the central PEG block and the two polyester blocks (ratio of blocks determined with NMR).

The block ratio as used herein is the weight ratio of the PLCA-blocks to the PEG-block (of known molecular weight) and can be calculated from grams of monomers (lactide+caprolactone) divided by grams of PEG used to synthesize the tri-block copolymer. Final tri-block composition after polymer purification was checked with $^1$H NMR by comparing integrals of peaks due to PEG and incorporated ring-opened monomers. The weight ratio of ε-caprolactone to L-lactide can be calculated from $^1$H NMR by comparing integrals of peaks due to ring-opened lactide and caprolactone. The integrals of peaks due to acyl endgroup and PEG block were used to calculate the degree of modification (range 0-2, which corresponds to a degree of acylation of 0 to 100%).

Example 1: Preparation of the Tri-Block Copolymer #33: Acylated (C2-Modified) PLCA-PEG-PLCA Polyethyleneglycol (PEG 1500, 12.5 g, 8.3 mmol) and ca. 100 ml toluene were charged into a 250 ml three-neck round-bottom flask equipped with a magnetic stirring bar. Using a Dean-Stark device with a cooler on top, 40 ml of toluene was distilled off to remove water (from PEG) azeotropically by heating at 150° C. at atmospheric pressure (1 bar) under nitrogen.

After cooling down the solution to ca. 80-100° C., L-lactide (2.75 g, 19 mmol) and caprolactone (24.75 g, 217 mmol) were added. 40 ml of toluene was distilled off to dry the monomers by heating at 150° C. at atmospheric pressure. Ca. 20 ml of dry toluene was left in the flask for the polymerization.

After cooling down the mixture to ca. 80-100° C., tin(II) 2-ethylhexanoate (0.25 ml) was added through one of the necks.

Polymerization was carried out at 120° C. for 1 day under nitrogen atmosphere.

After cooling down to room temperature, ca. 70 ml dichloromethane and 5.6 ml triethylamine (40 mmol) were added. Subsequently, 2.5 ml acetyl chloride (33 mmol) was added slowly to the stirred solution, which was cooled with an ice bath. The acylation reaction was continued for a few hours after which dichloromethane was removed by rotavap, and ethyl acetate (ca. 100 ml) was added to the residue. Triethylamine salt was removed by (paper) filtration and the polymer dissolved in the clear filtrate was precipitated by addition of a mixture of hexane and diethyl ether. At ca. −20° C. (in freezer) the polymer product separated as a waxy solid from which non-solvents could be decanted easily. Finally, the precipitated polymer was dried in vacuo. Yield: ca. 37 g. The PLCA/PEG block ratio was around 2.2; the ε-caprolactone/lactide ratio was 9/1.

Example 2. Preparation of the Tri-Block Copolymer #27

In a manner similar to example 1 an acylated PLCA-PEG-PLCA tri-block was synthesized having a PLCA/PEG ratio of 1.8 and a caprolactone/lactide weight ratio 9/1. The differences with example 1 were: different PLCA/PEG ratio and different caprolactone/lactide weight ratio.

Example 3. Preparation of the Tri-Block Copolymer #17

In a manner similar to example 1 an acylated PLCA-PEG-PLCA tri-block was synthesized having a PLCA/PEG ratio of 1.8 and a caprolactone/lactide weight ratio 9/1. The difference with example 1 was: different PLCA/PEG ratio.

Example 4 Fully C2-Modified PLCA-PEG-PLCA (#21)

Polyethyleneglycol (PEG 1500, 10 g, 6.7 mmol) and ca. 110 ml toluene were charged into a 250 ml three-neck round-bottom flask equipped with a magnetic stirring bar. Using a Dean-Stark device with a condenser on top, 45 ml of toluene was distilled off to remove water (from PEG) azeotropically by heating at 150° C. at atmospheric pressure under nitrogen.

After cooling down the solution to ca. 80-100° C., L-lactide (2 g, 14 mmol) and caprolactone (18 g, 158 mmol) were added. 40 ml of toluene was distilled off to dry the monomers by heating at 150° C. at atmospheric pressure. Ca. 25 ml of dry toluene was left in the flask for the polymerization.

After cooling down the mixture to ca. 80-100° C., tin(II) 2-ethylhexanoate (0.2 ml) was added through one of the necks.

Polymerization was carried out at 120° C. for 1 day under nitrogen atmosphere.

After cooling down to room temperature, ca. 60 ml dichloromethane and 4.7 ml triethylamine (34 mmol) were added. Subsequently, 2 ml acetyl chloride (28 mmol) was added slowly to the stirred solution, which was cooled with an ice bath. The acylation reaction was continued for a few hours after which dichloromethane was removed by rotavap, and ethyl acetate (ca. 100 ml) was added to the residue. Triethylamine salt was removed by (paper) filtration and the polymer, which was dissolved in the clear filtrate was precipitated by addition of a (1:1) mixture of hexane and diethyl ether. At ca. −20° C. (in freezer) the polymer product separated as a waxy solid from which non-solvents could be decanted easily. Finally, the precipitated polymer was dried in vacuo. Yield: ca. 27 g.

The PLCA/PEG block ratio is around 2; caprolactone/lactide weight ratio 9/1. Degree of modification (from NMR) is ca. 2.

Example 5. Synthesis Comparative Tri-Block Copolymer U5

This is the polymer that is similar to the one mentioned in the examples of US2007/0265356 (same block ratio, but different caplac).

Polyethyleneglycol (PEG 1500, 12.5 g, 8.3 mmol) and ca. 125 ml toluene were charged into a 250 ml three-neck round-bottom flask equipped with a magnetic stirring bar. Using a Dean-Stark device with a condenser on top, 60 ml of toluene was distilled off to remove water (from PEG) azeotropically by heating at 150° C. at atmospheric pressure under nitrogen.

After cooling down the solution to ca. 80-100° C., L-lactide (3 g, 21 mmol) and caprolactone (12 g, 105 mmol) were added. 40 ml of toluene was distilled off to dry the monomers by heating at 150° C. at atmospheric pressure. Ca. 25 ml of dry toluene was left in the flask for the polymerization.

After cooling down the mixture to ca. 80-100° C., tin(II) 2-ethylhexanoate (0.2 ml) was added through one of the necks.

Polymerization was carried out at 120° C. for 1 day under nitrogen atmosphere.

After cooling down to room temperature, ca. 50 ml dichloromethane and 2.5 ml triethylamine (18 mmol) were added. Subsequently, 2.1 ml hexanoyl chloride (15 mmol) was added slowly to the stirred solution, which was cooled with an ice bath. The acylation reaction was continued for a few hours after which dichloromethane was removed by rotavap, and ethyl acetate (ca. 100 ml) was added to the residue. Triethylamine salt was removed by (paper) filtration and the polymer, which was dissolved in the clear filtrate was precipitated by addition of a (1:1) mixture of hexane and diethyl ether. At ca. −20° C. (in freezer) the polymer product separated as a waxy solid from which non-solvents could be decanted easily. Finally, the precipitated polymer was dried in vacuo. Yield: ca. 27 g.

The PLCA/PEG block ratio of the comparative U5 block copolymer is around 1.2; caprolactone/lactide weight ratio 4/1. Degree of modification (from NMR) is ca. 1.7

Properties of the polymer are listed in table 1 below.

Example 6 Release of Model Drugs in PBS

This example illustrates the release profile of water soluble and hydrophobic model drugs from tri-block copolymer solutions of the present invention.

The following water soluble model proteins were used:

(1) IgG antibody (Sigma); this is a protein of around 150 kDa and has a solubility in water is above 10000 μg/ml.

(2) bovine serum albumin (Sigma); this is a protein of around 40 kDa and has a solubility in water of above 10000 μg/ml.

(3) lysozyme (Sigma); this is a protein of around 16 kDa and has a solubility in water of above 10000 μg/ml.

The following small molecules were used:

(1) celecoxib (LC Laboratories); this is a non-steroidal anti-inflammatory drug of 386 g/mol and has a solubility in water below 1 ug/ml (2) triamcinolone acetonide (Sigma); this is a corticosteroid and has a solubility in water below 20 ug/ml (3) iobitridol (Guerbet); this is a contrast agent of around 700 g/moland has a solubility in water above 5000 ug/ml.

The following peptide was used:

(1) Cyclosporin A (Sigma); this is a non-natural cyclic peptideof around 1000 g/mol amd has a solubility is water below 5 ug/ml Polymer solutions were prepared with the tri-block copolymers described in Table 1. The tri-block copolymers were weighted in 7-ml glass vial and melted at 50° C. using a water bath. Protein stock solutions in PBS (phosphate buffer saline; B. Braun, 10 mM, pH=7.4) were added to the molten polymer to achieve the required polymer content in the solutions containing 1% (w/v) protein. The mixtures of protein, tri-block copolymer and PBS were vortexed for 1 min and placed on a rotating wheel at 4° C. overnight.

For the hydrophobic drugs, a mixture drug/polymer was first prepared in ethylaacetate. Ethylacetate was evaporated and PBS was added.

With a syringe, 300 μl of the solutions were placed in glass vials (8.2×40 mm). The glass vials were incubated for 30 min at the required release temperature to allow gelation. Pre-heated PBS was added on top of the gel. At regular time intervals, the buffer was removed, followed by the addition of fresh PBS. The removed buffer samples were analyzed for

TABLE 1

Characteristics of tri-block copolymers #33, #27, #21, #17 and U5

| Tri-block copolymer | Block ratio (PLCA/PEG ratio) | Weight ratio of ε-caprolactone to lactide (cap/lac ratio) | Mn as determined using $^1$H NMR | End-group | Degree of acylation (degree of modification, DM) (%) |
|---|---|---|---|---|---|
| Comparative U5 polymer | 1.2 | 4/1 | 3300 | Hexanoyl (C6) | 75 |
| PLCA/PEG2.2-CL/LA 4/1-C2 (#17) | 2.2 | 4/1 | 5300 | Acetyl (C2) | 100 |
| PLCA/PEG2.0-CL/LA 9/1-C2 (#21) | 2.0 | 9/1 | 4700 | Acetyl (C2) | 100 |
| PLCA/PEG1.8-CL/LA 9/1-C2 (#27) | 1.8 | 9/1 | 4200 | Acetyl (C2) | 100 |
| PLCA/PEG2.2 CL/LA 9/1-C2 (#33) | 2.2 | 9/1 | 5300 | Acetyl (C2) | 100 | their protein content by either UPLC (for BSA and lysozyme) or bicinchoninic acid assay (BCA®) protein assay (for IgG).

IgG was analysed by BCA® protein assay: IgG release samples (25 μL) were pipetted into a 96-microwells plate and 200 μL of working reagent (BCA reagent A: BCA reagent B, 50/1 v/v) was added. After incubation of the plates for 30 minutes at 37° C., the absorbance was measured at 550 nm with a Novapath™ Microplate Reader (Bio-Rad). Standard protein solutions (concentration range: 0.01-1 mg/mL) were prepared to generate a calibration line.

BSA was analysed by UPLC: BSA release samples were analyzed using a Waters Acquity™ Ultra Performance LC system equipped with an Acquity™ BEH300 C18 1.7 μm column (5 cm), a binary solvent manager, a sample manager with column oven at 50° C. and an Acquity™ TUV detector (detection wavelength: 210 nm). After injection of 5 μL release sample, a gradient was run from 80% A (H2O/ACN 95/5 (% v/v) containing 0.1% TFA) to 60% B (100% ACN with 0.1% TFA) in 2 minutes at a flow rate of 0.25 mL/min. Standard protein solutions (concentration range: 0.01-1 mg/mL) were used to obtain a calibration line.

Lysozyme was analysed by UPLC: lysozyme release samples were analyzed using a Waters Acquity™ Ultra Performance LC system equipped with an Acquity™ BEH300 C18 1.7 μm column (5 cm), a binary solvent manager, a sample manager with column oven at 50° C. and an Acquity™ TUV detector (detection wavelength: 280 nm). After injection of 5 μL release sample, a gradient was run from 75% A (H2O/ACN 95/5 (% v/v) containing 0.1% TFA) to 40% B (100% ACN with 0.1% TFA) in 4 minutes at a flow rate of 0.25 mL/min. Standard protein solutions (concentration range: 0.01-1 mg/mL) were used to obtain a calibration line.

Celecoxib was analysed by UPLC: Celecoxib concentration in the buffer was measured by a Waters Acquity™) Ultra Performance LC system (UPLC, Waters, Milford Mass., USA) equipped with an Acquity™ BEH C18 1.7 μm column (2.1×100 mm), a binary solvent manager, a sample manager with column oven at 50° C. and an Acquity™ TUV Detector (detection wavelength: 254 nm). After injection of 7.5 μl release sample, a gradient was run from 100% A (H2O/ACN 95/5% (v/v) containing 0.1% TFA) to 100% B (MeOH/ACN/H2O 45/45/10% (v/v) containing 0.1% TFA) in 2 minutes and kept at 100% B from 10 min at a flow rate of 0.08 ml/min. The run time was 16 min. A calibration curve was obtained after injection of standard celecoxib solutions in DMSO (0.5-100 ug/ml). The chromatograms were analused using Empower Software Version 1154 (Waters, Milford Mass., USA). CLB concentration in the release sample was in the range 5-20 μg/ml.

Triamcinolone acetonide (TA) was analysed by UPLC: TA concentration in the buffer was measured by a Waters Acquity™ Ultra Performance LC system (UPLC, Waters, Milford Mass., USA) equipped with an Acquity™ BEH C18 1.7 μm column (2.1×50 mm), a binary solvent manager, a sample manager with column oven at 50° C. and an Acquity™ TUV Detector (detection wavelength: 240 nm). After injection of 7.5 μl release sample, a gradient was run from 50% A (H2O/ACN 95/5% (v/v) containing 0.1% TFA) to 80% B (ACN/H2O 95/10% (v/v) containing 0.1% TFA) in 1.5 minutes at a flow rate of 0.25 ml/min. The run time was 3.2 min. A calibration curve was obtained after injection of standard TA solutions in DMSO (0.5-100 ug/ml). The chromatograms were analused using Empower Software Version 1154 (Waters, Milford Mass., USA). TA concentration in the release sample was in the range 5-20 μg/ml.

Iobitriodol (ITD) was analysed by UPLC: ITD concentration in the buffer was measured by a Waters Acquity™) Ultra Performance LC system (UPLC, Waters, Milford Mass., USA) equipped with an Acquity™ HSS 1.7 μm column (2.1×50 mm), a binary solvent manager, a sample manager with column oven at 50° C. and an Acquity™ TUV Detector (detection wavelength: 204 nm). After injection of 7.5 μl release sample, a gradient was run from 100% A (H2O 2O containing 0.1% TFA) to 48% B (IPA containing 0.1% TFA) in 0.9 minutes at a flow rate of 0.25 ml/min. The run time was 2 min. A calibration curve was obtained after injection of standard ITD solutions in PBS (0.5-100 ug/ml). The chromatograms were analysed using Empower Software Version 1154 (Waters, Milford Mass., USA). ITD concentration in the release sample was in the range 5-20 μg/ml.

Cyclosporin A (CyA) was analysed by UPLC: CyA concentration in the buffer was measured by a Waters Acquity™) Ultra Performance LC system (UPLC, Waters, Milford Mass., USA) equipped with an Acquity™ BEH C4 1.7 μm column (2.1×50 mm), a binary solvent manager, a sample manager with column oven at 50° C. and an Acquity™ TUV Detector (detection wavelength: 220 nm). After injection of 7.5 μl release sample, a gradient was run from 100% A (H2O/ACN 95/5% (v/v) containing 0.1% TFA) to 100% B (ACN/H2O 95/10% (v/v) containing 0.1% TFA) in 1 minutes at a flow rate of 0.25 ml/min. The run time was 3.6 min. A calibration curve was obtained after injection of standard CyA solutions in DMSO (0.5-100 ug/ml). The chromatograms were analysed using Empower Software Version 1154 (Waters, Milford Mass., USA). CyA concentration in the release sample was in the range 5-20 μg/ml.

The results of this example are shown in FIGS. 1 to 4.

Example 7 Synthesis of B-A-B Block

The syntheses of the compositions were conducted as per Example 4.

TABLE 2

Characteristics of tri-block copolymers

| ID | Tri-block copolymer | Block ratio (PLCA/PEG ratio) | Weight ratio of caprolactone to lactide (cap/lac ratio) | End group | Degree of acylation/% |
|---|---|---|---|---|---|
| A | $PEG_{1500}(CAP_{90\%}/LAC_{10\%})_{1.8}(C_2)_{2.0}$ | 1.8 | 9/1 | Acetyl C2 | 100 |
| B | $PEG_{1500}(CAP_{90\%}/LAC_{10\%})_{2.0}(C_2)_{2.0}$ | 2.0 | 9/1 | Acetyl C2 | 100 |
| C | $PEG_{1500}(CAP_{90\%}/LAC_{10\%})_{2.2}(C_2)_{2.0}$ | 2.2 | 9/1 | Acetyl C2 | 100 |

TABLE 2-continued

Characteristics of tri-block copolymers

| ID | Tri-block copolymer | Block ratio (PLCA/PEG ratio) | Weight ratio of caprolactone to lactide (cap/lac ratio) | End group | Degree of acylation/% |
|---|---|---|---|---|---|
| D | $PEG_{1500}(CAP_{90\%}/LAC_{10\%})_{2.4}(C_2)_{2.0}$ | 2.4 | 9/1 | Acetyl C2 | 100 |
| E | $PEG_{1500}(CAP_{90\%}/LAC_{10\%})_{2.6}(C_2)_{2.0}$ | 2.6 | 9/1 | Acetyl C2 | 100 |
| F | $PEG_{1500}(CAP_{90\%}/LAC_{10\%})_{2.8}(C_2)_{2.0}$ | 2.8 | 9/1 | Acetyl C2 | 100 |
| G | $PEG_{1500}(CAP_{90\%}/LAC_{10\%})_{2.0}(C_2)_{0}$ | 2.0 | 9/1 | — | 0 |
| H | $PEG_{1500}(CAP_{90\%}/LAC_{10\%})_{2.0}(C_2)_{1}$ | 2.0 | 9/1 | Acetyl C2 | 50 |
| I | $PEG_{1500}(CAP_{90\%}/LAC_{10\%})_{1.2}(C_2)_{2.0}$ | 1.2 | 9/1 | Acetyl C2 | 100 |
| J | $PEG_{1500}(CAP_{80\%}/LAC_{20\%})_{1.2}(C_6)_{2.0}$ | 1.2 | 4/1 | Hexanoyl C6 | 100 |
| K | $PEG_{2000}(CAP_{80\%}/LAC_{20\%})_{1.2}(C_6)_{2.0}$ | 1.2 | 4/1 | Hexanoyl C6 | 100 |

Example 8 Degradation of Hydrogel Compositions with Varying PEG/PLCA Ratios

This example shows the degradation profiles for compositions according to the invention. Typically, gels were cast from 20 wt % polymers solution with 3 wt % lysozyme in small vials and allowed to gel at 37° C. PBS buffer was added and replaced periodically. The wet gels were weighed and the amount of lysozyme released was determined by the BOA® assay and/or UPLC (BOA® and UPLC were conducted as per example 6). The enzymatic activity of lysozyme was determined by the hydrolysis of the outer cell membrane of *Micrococcus Lysodeikticus*.

Tri-block copolymers Z1-Z3 were synthesised in a manner similar to examples 2 and 4.

20% solutions of the tri-block copolymers of Table 4 in PBS were prepared and placed in an oven at 37° C. for thermogelations. The forming of the gel was checked after 1 hour and gels were formed for compositions comprising tri-block copolymers comprising A, B, Z1, Z2 and Z3. After longer periods of time (several hours) also Z3 showed phase separation and after even longer periods Z2 and Z1 also showed phase separation. Phase separation was not observed for compositions comprising tri-block copolymers A and B.

TABLE 3

Degradation of the B-A-B tri-block copolymers

| | | Unloaded gels | | Protein-loaded gels[1] | |
|---|---|---|---|---|---|
| ID | Structure | at 20 wt % | at 25 wt % | BSA | Lysozyme |
| I | $PEG_{1500}(CAP_{90\%}/LAC_{10\%})_{1.2}(C_2)_{2.0}$ | COMPARATIVE EXAMPLE: does not form a gel at 37° C. | | | |
| A(#27) | $PEG_{1500}(CAP_{90\%}/LAC_{10\%})_{1.8}(C_2)_{2.0}$ | 8 days | 14 days | 6 days | 6 days |
| B (#21) | $PEG_{1500}(CAP_{90\%}/LAC_{10\%})_{2.0}(C_2)_{2.0}$ | 27 days | 31 days | 21 days | 19 days |
| C (#33) | $PEG_{1500}(CAP_{90\%}/LAC_{10\%})_{2.2}(C_2)_{2.0}$ | 31 days | 34 days | 12 days | 12 days |
| D | $PEG_{1500}(CAP_{90\%}/LAC_{10\%})_{2.4}(C_2)_{2.0}$ | 34 days | 34 days | 11 days | 12 days |
| E | $PEG_{1500}(CAP_{90\%}/LAC_{10\%})_{2.6}(C_2)_{2.0}$ | 250 days | 250 days | 12 days | 12 days |
| F | $PEG_{1500}(CAP_{90\%}/LAC_{10\%})_{2.8}(C_2)_{2.0}$ | COMPARATIVE EXAMPLE: does not dissolve in PBS | | | |

Example 8b

TABLE 4

Different end-groups

| ID | Tri-block copolymer | Block ratio (PLCA/PEG ratio) | Weight ratio of caprolactone to lactide (cap/lac ratio) | End group | Degree of acylation/% |
|---|---|---|---|---|---|
| Z1 | PEG1500(CAP90%/LAC10%)1.8(C3)2.0 | 1.8 | 9/1 | C3 | 100 |
| Z2 | PEG1500(CAP90%/LAC10%)2(C3)2.0 | 2 | 9/1 | C3 | 100 |
| Z3 | PEG1500(CAP90%/LAC10%)1.8(C4)2.0 | 1.8 | 9/1 | C4 | 100 |
| A | PEG1500(CAP90%/LAC10%)1.8(C2)2.0 | 1.8 | 9/1 | Acetyl C2 | 100 |
| B | PEG1500(CAP90%/LAC10%)2.0(C2)2.0 | 2.0 | 9/1 | Acetyl C2 | 100 |

Example 9 Release of Model Protein Vs PCLA/PEG Ratio

This example illustrates the release profile of water soluble model proteins from tri-block copolymer solutions of the present invention.

The method for detecting release of the drug from the compositions was followed as per example 2. Burst release was calculated by plotting the cumulative release versus $t^{0.5}$. The degradation experiments were conducted as per example 2. The results are presented in Table 4.

TABLE 5

Characteristics of tri-block copolymers with varying weight ratio ε-caprolactone to lactide

| ID | Structure | Weight ratio ε-caprolactone to lactide | Degradation Time | Release of water soluble model protein | Burst release |
|---|---|---|---|---|---|
| M | PEG$_{1500}$(CAP$_{100\%}$/LAC$_{0\%}$)$_{1.8}$(C$_2$)$_{2.0}$ | 1/0 ε-caprolactone | >140 days | ~25 days | 1.8% |
| N | PEG$_{1500}$(CAP$_{95\%}$/LAC$_{5\%}$)$_{2.0}$(C$_2$)$_{2.0}$ | 19/1 | >50 days | ~25 days | 1.6% |
| B(21) | PEG$_{1500}$(CAP$_{90\%}$/LAC$_{10\%}$)$_{2.0}$(C$_2$)$_{2.0}$ | 9/1 | ~42 days | ~30 days | 1.0% |
| O | PEG$_{1500}$(CAP$_{80\%}$/LAC$_{20\%}$)$_{2.0}$(C$_2$)$_{2.0}$ | 4/1 | ~23 days | ~16 days | 4.9% |
| P | PEG$_{1500}$(CAP$_{50\%}$/LAC$_{50\%}$)$_{2.0}$(C$_2$)$_{2.0}$ | 1/1 | ~22 days | ~9 days | 5.0% |

Example 10 Rheology of Compositions with Different End Caps

Composition B (#21) from experiment 9 (which had the minimum burst release profile) was compared by rheological analysis, to the compositions with the same PLCA/PEG ratio but with different degrees of end acylation.

Rheological characterization of the blends was done with a AR-G2 rheometer (TA Instruments, Etten-Leur, The Netherlands) equipped with a 1° steel cone geometry of 20 mm diameter and solvent trap. Polymer blend solutions of 20% (w/w) were prepared in PBS pH 7.4 at 4° C. 300 μl of the solutions were placed in glass vial (8.2×40 mm) and incubated for around 3 hours at 37° C. to enable gelation and stabilization. Using a spatula, approximately 70 mg of the sample was placed between the pre-heated (37° C.) plates of the rheometer. Rheological gel characteristics were monitored by oscillatory time sweep experiments. During time sweep experiments G'(shear storage modulus) and G" (loss modulus) were measured for a period of 5 min. Also temperature sweep experiments were performed on the polymer solutions. Therefore the plates of the rheometer were pre-cooled at 4° C. Temperature increase was 1° C./min. When G"/G' (=tan δ)=1, the sample is considered as a gel in a rheological point of view. All experiments were performed at constant strain (1%) and frequency (1 Hz).

The results are shown in Table 6

TABLE 6

Gel characteristics for compositions B and F

| | Composition | Gel at 37° C. | Degree of acylation/% |
|---|---|---|---|
| B | 21 | YES | 100 |
| F | PEG$_{1500}$(CAP$_{90\%}$/LAC$_{10\%}$)$_{2.0}$(C$_2$)$_1$ | YES | 50 |

Example 11 Degradation of Compositions of Tri-Block Copolymers of the Invention with Different Degrees of Acylation This example illustrates the degradation profile for tri-block copolymers of the invention compared to a model compound that is not acylated. In this example 300 mg of a formulation containing 20% tri-block copolymer and 3 wt % lysozyme was prepared. The procedure was followed according to example 8.

The results are shown in FIG. 5 and summarized in Table 7.

TABLE 7

Degradation times for tri-block copolymers

| ID | Polymer composition | Degradation time | Degree of acylation/% |
|---|---|---|---|
| F | PEG1500(CAP90%/LAC10%)$_{2.0}$(C2)$_0$ | 14 days | 0 |
| G | PEG1500(CAP90%/LAC10%)$_{2.0}$(C2)$_1$ | 14 days | 50 |
| B | PEG1500(CAP90%/LAC10%)$_{2.0}$(C2)$_2$ | 42 days | 100 |

Example 12 Release of Lysozyme

This example shows the release profile of lysozyme which was used as a model water soluble protein, from compositions of the invention compared to a composition comprising a tri-block copolymer that is not acylated.

The procedure was followed as per example 6.

The results are shown in FIG. 6 and summarized in Table 8.

TABLE 8

Comparison of controlled release profile for tri-block copolymers with different degrees of acylation.

| ID | Composition | Degree of acylation/% | Controlled burst release* |
|---|---|---|---|
| F | PEG$_{1500}$(CAP$_{90\%}$/LAC$_{10\%}$)$_{2.0}$(C$_2$)$_0$ | 0 | -- |
| G | PEG$_{1500}$(CAP$_{90\%}$/LAC$_{10\%}$)$_{2.0}$(C$_2$)$_1$ | 50 | + |
| B | PEG$_{1500}$(CAP$_{90\%}$/LAC$_{10\%}$)$_{2.0}$(C$_2$)$_2$ | 100 | ++ |

-- very large Durst release
– large burst release
+ small burst release
++ very small burst release

Example 13 Mathematical Analysis of Release Profiles

The data from the release experiment (example 12) was plotted against the square root of the time of release. The data was fitted using linear regression analysis and the burst release could be determined by extrapolating the lines of best fit to the y axis. The point where the extrapolated line crosses the y axis gives the value for percentage burst release. The results are shown in FIG. 7.

Example 14 Synthesis of Iodine Functionalized Tri-Block Copolymers

This example details a method to covalently bond a radiopaque atom to a tri-block copolymer. The structure of a tri-block copolymer which is acylated is given below in formula (1).

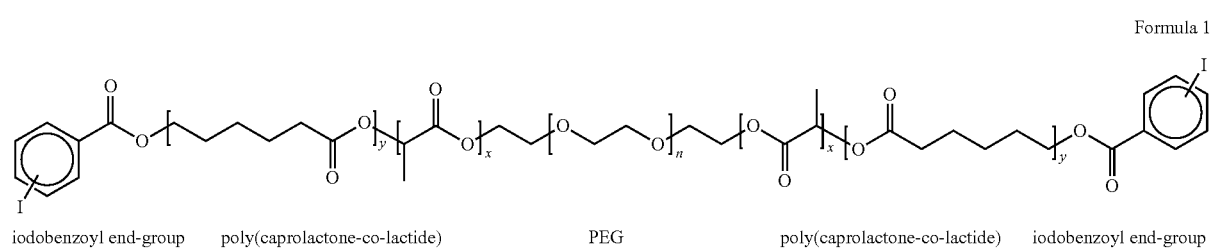

Formula 1 iodobenzoyl end-group    poly(caprolactone-co-lactide)    PEG    poly(caprolactone-co-lactide)    iodobenzoyl end-group The synthesis of tri-block copolymers wherein at least part of the hydroxyl end-groups of the tri-block copolymer are covalently bound to a compound containing radiopaque atoms was done according to the method previously described in US7740877, examples 1, 2 and 3. The synthesis led to tri-block copolymers (Table 9) with triiodobenzoyl groups (1.8 groups per chain) as confirmed by 1H NMR.

TABLE 9

Tri-block copolymers used.

| ID | ID | PLCA/PEG | Caprolactone/lactide | Degree of acylation (%) | End-group | Number average mol. weight PEG |
|---|---|---|---|---|---|---|
| P (#81) | I-Gell ® #1 | 1.8 | 9/1 | 90% | Triiodobenzoyl | 1500 |
| Q (#29) | I-Gell ® #2 | 1.0 | 9/1 | 90% | Triiodobenzoyl | 1500 |

In the following examples different compositions comprising P and Q were made and the compositions are summarized in Table 10.

TABLE 10

Overview of compositions used in examples 15-19

| Example | Tri-block copolymer (wt %) | | |
|---|---|---|---|
|  | P | Q | 17 |
| 15 | — | — | 100 |
| 16 | 25 | — | 75 |
|  | 30 | — | 70 |
|  | 50 | — | 50 |
|  | 70 | — | 30 |
| 17 a | 30 | — | 70 |
| b | — | 30 | 70 |
| 18 a | — | — | 100 |
| b | 25 | — | 75 |
| 19 a | 25 | — | 75 |
| b | 50 | — | 50 |

Example 15 Loading of a Tri-Block Copolymer Composition with Contrast Agent Hexabrix™

In order to achieve prolonged release of a pharmaceutically active ingredient, retention in the treatment location (for example a joint) must be maintained for a minimum of 4 weeks. To determine this retention time the tri-block copolymer composition must be visualized. This example shows how loading a tri-block copolymer with a conventional contrast agent does not achieve this goal.

Polymer #17 (see Table 1) was loaded with 15% Hexabrix™ (Guerbet). Hexabrix™ contrast agent is a low osmolar ionic dimer. Each milliliter contains 393 mg of ioxaglate meglumine, 196 mg of ioxaglate sodium and 0.10 mg of edetate calcium disodium as a stabilizer. The solution contains 3.48 mg (0.15 vmEq) sodium in each milliliter and provides 32% (320 mg/mL) organically bound iodine.

The commercially available Hexabrix™ solution was diluted with phosphate buffer (50 mM phosphate, pH 7.4, 0.07 mM NaCl) at a ratio 15/85 v/v. This diluted Hexabrix™ solution was used to dissolve the polymer, leading to the preparation of a formulation containing 25 wt % polymer with respect to buffer and Hexabrix™. Each gram of formulation contained 44 mg ioxaglate meglumine.

The loaded tri-block copolymer composition was injected into a chicken knee and visualized using microCT (Skyscan model 1076, Skyscan, Kontich, Belgium) Scans were performed using the following scanner settings: isotropic voxelsize of 35 mm, at a voltage of 55 kV, a current of 170 mA, field of view of 35 mm, and a 0.5 mm aluminium filter, over 198° with a 0.8 rotation step. 1 hour after injection the visibility of the gel was diminished and a further 1 day later the composition could not be visualized. Make table T=0-1-24 hrs showing 100%-50%-0% visualization as relative grey value The results are also indicated in Table 11.

TABLE 11

Image-retention of Polymer #17 (25% w/w) loaded with 15% Hexabrix

| Time point in hours | Relative grey surface area |
|---|---|
| T = 0 | 100% |
| T = 1 | 50% |
| T = 24 | 0% |

Example 16 Radiopaque Tri-Block Copolymer Compositions

This example shows that a tri-block copolymer wherein at least part of the hydroxyl end-groups of the tri-block copolymer are covalently bound to a compound containing radiopaque atoms can be visualized by microCT. (Skyscan model 1076, Skyscan, Kontich, Belgium) Scans were performed using the following scanner settings: isotropic voxelsize of 35 mm, at a voltage of 55 kV, a current of 170 mA, field of view of 35 mm, and a 0.5 mm aluminium filter, over 198° with a 0.8 rotation step. Scan time was 10 minutes. In this example different compositions were prepared comprising different weight percentages of tri-block copolymers (Table 10, example 16) wherein the hydroxyl end-groups of the tri-block copolymer are at least partially acylated with an acetyl group or wherein at least part of the hydroxyl end-groups of the tri-block copolymer are covalently bound to a compound containing radiopaque atoms.

The compositions (Table 10, examples 16) were prepared as follows. Both polymers P and #17 were separately dissolved in ethylacetate at a concentration of 500 mg/mL. The solutions were mixed at the desired ratios and the mixtures were transferred into petri dishes. The solvent was removed under nitrogen flow for 48 hours. To 500 mg polymer blend, phosphate buffer (50 mM, 0.07 mM NaCl, 0.02% NaN3, pH 7.4) was added to yield solutions at 25 wt %. The compositions were measured in glass vials and the X-ray intensity plotted on a graph (FIG. 8). The compositions were measured in glass vials and the X-ray intensity plotted on a graph (FIG. 8).

Example 17 CT Imaging in Radiopaque Tri-Block Copolymer Compositions

This example shows the CT visualization times for different mixtures of tri-block copolymers.

The mixtures of copolymers (Table 10, example 17a and 17b) were prepared, injected into the knee of a rat cadaver and visualized by microCT (Skyscan model 1076, Skyscan, Kontich, Belgium). Scans were performed using the following scanner settings: isotropic voxelsize of 35 mm, at a voltage of 55 kV, a current of 170 mA, field of view of 35 mm, and a 0.5 mm aluminium filter, over 198° with a 0.8 rotation step. The results are shown in Table 14.

The composition 17a was visible for only a few days whereas composition 17b was visible for 3 weeks (FIG. 11).

Example 18 Release Profiles of Tri-Block Copolymers Wherein the End Groups are Acylated or are Radiopaque Substituted Acyl Groups This example illustrates the release profile of a pharmaceutically active ingredient from tri-block copolymer compositions and also the degradation profiles for tri-block copolymer compositions comprising a pharmaceutically active ingredient.

OAc-Gell (#17) and a mixture of a I-Gell®#1 (P) and OAc-Gell (#17) were prepared at 25 wt % in 50 mM phosphate buffer at pH 7.4, 0.42% NaCl and 0.05% NaN3. The loading of Celecoxib was 1.25 mg/mL. Release experiments were performed as per example 6 and at 37° C. in PBS buffer containing 0.2% Tween 80. Error bars represent standard error of the mean (n=6). The results are shown in FIG. 9 and summarized in Table 12.

TABLE 12

Overview release time and erosion profile for examples 18a and 18b.

| Example | Release time | Erosion time (solid content) |
|---|---|---|
| 18a | 28 | 28 |
| 18b | 35 | 35 |

Wet weight=weight of the depots, as measured by decanting the PBS buffer and weighing the remaining gel, after which the original vial-weight is subtracted Dry weight=weight of the freeze dried depots after decanting of the buffer (i.e. polymer weight) and subtracting the weight of the vial Solid content=polymer concentration in the depots (dry weight/wet weight)

Example 19 Degradation Profile for Tri-Block Copolymer Compositions

This example shows the in vivo degradation profile for compositions of tri-block copolymers wherein at least part of the hydroxyl end-groups of the tri-block copolymer are covalently bound to a compound containing radiopaque atoms.

Compositions (Table 10, example 19a and 19b) were prepared were prepared by dissolving 25 wt % tri-block copolymer (comprising 75% P and 25% #17, or 50% P and 50% #17) in 75% PBS buffer, pH 7.4. 50 mM, 0.15% NaCl of the composition was injected subcutaneously into rats knees. The injected volume of 19b was then visualized and measured using 3D micro-CT imaging (Skyscan model 1076, Skyscan, Kontich, Belgium). The rats were anesthetized using Isoflurane and then placed in a custom made scanner bed, fixing the hind limb in an extended position. Scans were performed using the following scanner settings: isotropic voxel size of 35 mm, at a voltage of 55 kV, a current of 170 mA, field of view of 35 mm, and a 0.5 mm aluminium filter, over 198° with a 0.8 rotation step. The rat knees and subcutaneous depots were scanned on days 0, 1, 4 and 8 and after that weekly until the gel was no longer visible. The scan time was 16 minutes and a frame averaging of 3 was used. Images obtained using the uCT scanner were reconstructed using Skyskan analysis software. The datasets were segmented using a fixed attenuation threshold between air and subchondral bone. Subsequently, regions of interest were drawn around the patellar cartilage and attenuation and volume were calculated. The injected volume of 19a (non-radiopaque), was monitored through the skin with a measuring caliper. The results are shown in FIG. 10 and summarized in Table 13 and 14.

TABLE 13

Overview of erosion monitoring for examples 19a and 19b.

| | 19a | | 19b | |
|---|---|---|---|---|
| Day | Observations | Surface area/% | Observations | Surface area/% |
| 0 | Distinct oval shape, sharp edges | 100 | Higher intensity than for 19a | 100 |
| 4 | Sharp edges maintained | 80 | | 70 |
| 8 | Less sharp edges on interior side | 40 | | 65 |
| 14 | Fractured shape - small light spots in dark area | 10 | | 75 |
| 21 | Not visible | — | | 50 |
| 40 | — | — | Still visible | 40 |

Surface area=relative area with respect to surface area at t=0 (set to 100%)

TABLE 14

Overview of compositions and microCT characteristics for examples 15-19

| | Tri-block copolymer (wt %) | | | Duration of visibility | Active |
|---|---|---|---|---|---|
| Example | P | Q | 17 | in micro CT | ingredient |
| 15 | — | — | 100 | <24 hours | Hexabrix ™ |
| 16 a | 25 | — | 75 | All visible in micro CT but duration of visibility not measured | — |
| | 30 | — | 70 | | — |
| | 50 | — | 50 | | — |
| | 70 | — | 30 | | — |
| 17 a | 30 | — | 70 | <7 days | — |
| b | — | 30 | 70 | ~4 weeks | — |
| 18 a | — | — | 100 | — | Celecoxib |
| b | 25 | — | 75 | — | Celecoxib |
| 19 a | 25 | — | 75 | ~40 days | — |
| b | 50 | — | 50 | ~77 days | — |

Discussion and Conclusion

BRIEF DESCRIPTION OF THE FIGURES

In FIG. 1, the following legend is used:
Release from U5: Lysozyme (diamonds), ibitridol (circles), Triamcinolone acetonide (squares), Cyclopsorin A (open squares), celecoxib (open triangles)

In FIG. 5 the compositions used are
G PEG1500(Cap90%/Lac10%)2.0 (triangle)
H PEG1500(Cap90%/Lac10%)2.0(C2)1 (diamond)
B (#21): PEG1500(Cap90%/Lac10%)2.0(C2)$_2$ (square)

In FIG. 6 the compositions used are
G PEG1500(Cap90%/Lac10%)2.0 (triangle)
H PEG1500(Cap90%/Lac10%)2.0(C2)1 (diamond)
B (#21): PEG1500(Cap90%/Lac10%)2.0(C2)$_2$ (square)

In FIG. 7 the compositions used are
G PEG1500(Cap90%/Lac10%)2.0 (triangle)
H PEG1500(Cap90%/Lac10%)2.0(C2)1 (diamond)
B (#21): PEG1500(Cap90%/Lac10%)2.0(C2)$_2$ (square)

Figure 1:
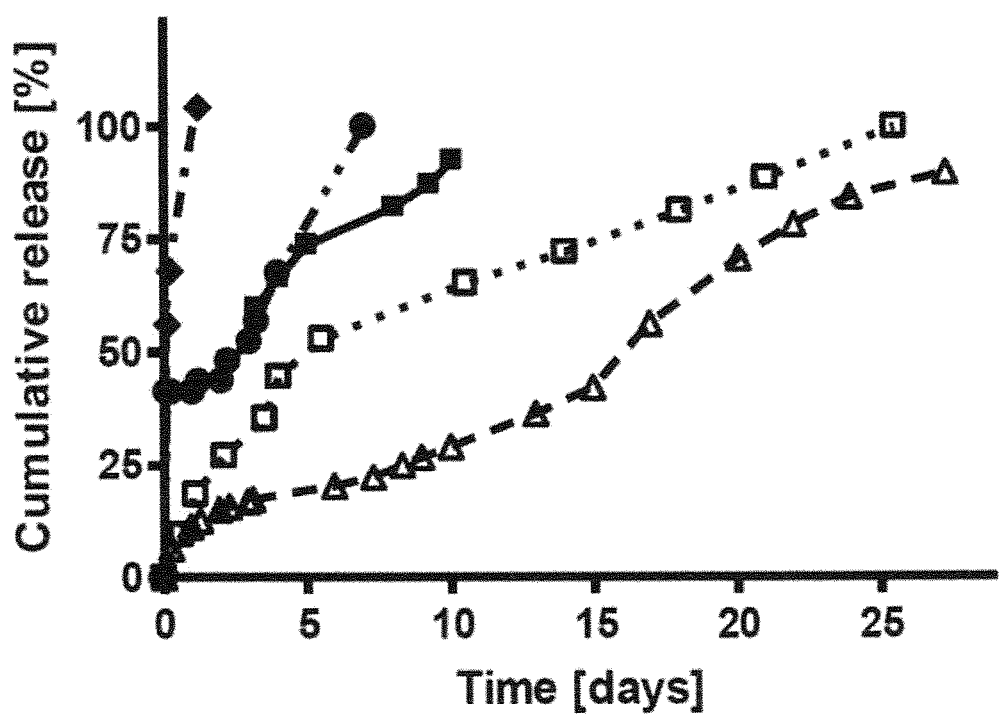
FIG. 1 shows the release of both hydrophobic-type (celecoxib (CLB), triamcinolone (TA), cyclosporine A (cya) and water soluble (iobitrodol (ITD) and lysozyme (Lys)) active ingredients from 25% w/w U5 (low PLCA/PEG ratio) based on PBS and active ingredient at 37° C. The comparative U5 polymer that phase separates at 37° C.

As can be seen from FIG. 1, the tri-block copolymer with a low PLCA/PEG ratio of 1.2 maybe be employed to obtain long-term controlled release of hydrophobic molecules (celecoxib, triamcinolone acetonide, cyclosporin A) without burst; whereas that polymer is not suitable to prevent burst release of water soluble molecules (lysozyme, iobitrodol) and as such not suitable for use in the composition of the present invention.

Figure 2:
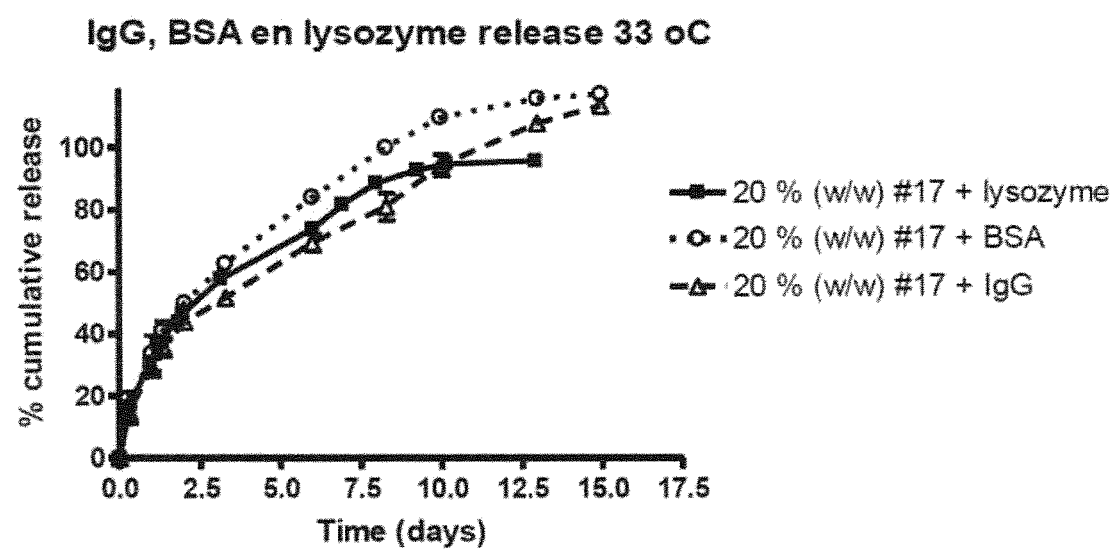
FIG. 2 shows the release of IgG, BSA and lysozyme from a solution of 20% w/w tri-block copolymer #17 based on the amount of solvent and pharmaceutically active ingredient present in the composition at 33° C. Data are shown as average±standard deviation (n=3).

As can be seen from FIG. 2, the tri-block copolymer #17 may be employed in the composition of the invention to get controlled release without too much burst release of water soluble model proteins IgG; BSA and lysozyme.

Figure 3:
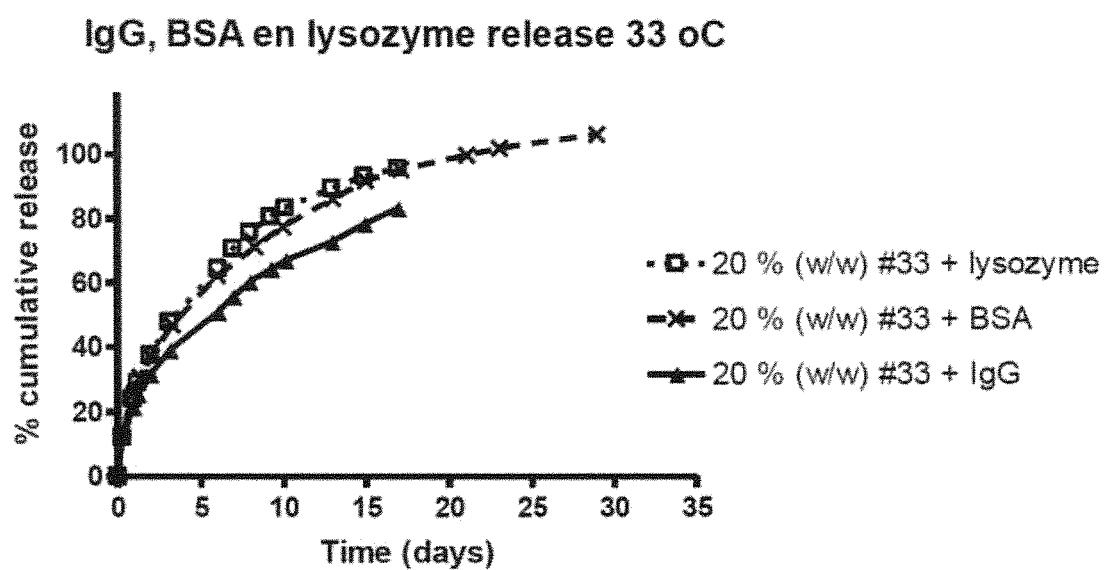
FIG. 3 shows the release of IgG, BSA and lysozyme from a solution of 20% w/w tri-block copolymer #33 based on the amount of solvent and pharmaceutically active ingredient present in the composition at 33° C.

As can be seen from FIG. 3, the tri-block copolymer #33 may be employed to get a controlled release without too much burst release of the water soluble pharmaceutically active ingredients (in this case Lysozyme, BSA and IgG).

Figure 4:
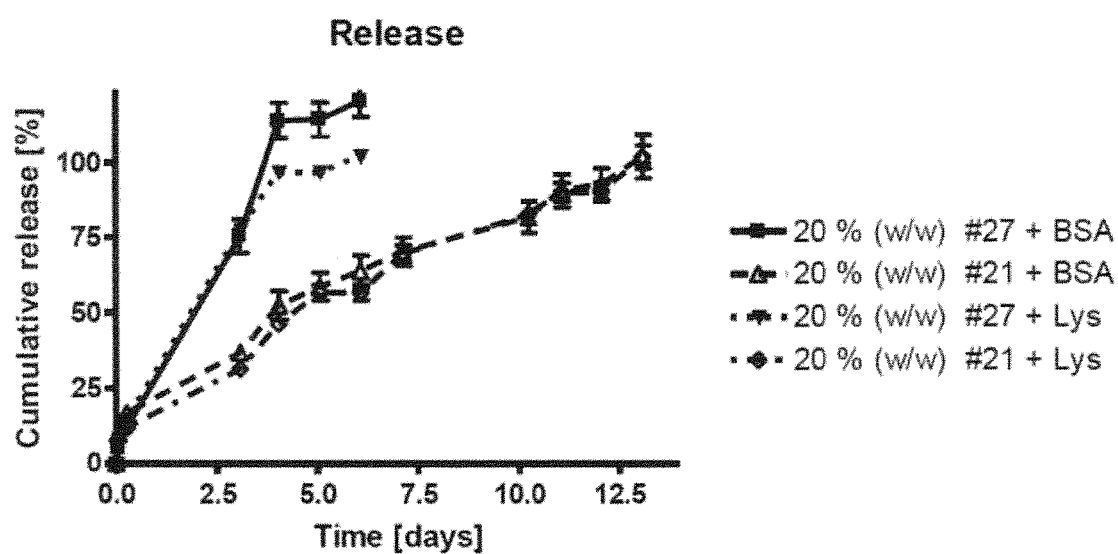
FIG. 4 shows the release of model proteins lysozyme, BSA and IgG from tri-block copolymers #27 and from #21 at 37° C. at a concentration of 20% w/w tri-block copolymer based on the amount of solvent and pharmaceutically active ingredient present in the composition. Data are shown as average±standard deviation (n=3).

As can be seen from FIG. 4, the tri-block copolymers #21 and #27 are suitable for the controlled release of the tested model proteins: lysozyme and BSA.

The results in Table 3 show that at a block ratio of lower than 1.4, the tri-block co-polymer does not form a gel whereas at a block ratio of above 2.6, the tri-block co-polymer does not dissolve in the buffer solution.

The gel behaviour for the compositions shown in Table 4 indicate that preferably for release of water soluble proteins, the hydroxyl end-groups of the tri-block copolymer in the composition of the invention are at least partially acylated with an optionally substituted acetyl, an optionally substituted propionyl, an optionally substituted butyl, or an optionally substituted benzoyl group. Preferably, the hydroxyl end-groups of the tri-block copolymer in the composition of the invention are at least partially acylated with an optionally substituted acetyl or an optionally substituted propionyl. More preferably, the hydroxyl end-groups of the tri-block copolymer in the composition of the invention are at least partially acylated with an optionally substituted acetyl or an optionally substituted propionyl, most preferably with an optionally substituted acetyl.

As can be seen from Table 5 longer degradation and release are obtained for tri-block copolymers having a weight ratio of ε-caprolactone to lactide of at least 9/1. Furthermore it can be seen that a tri-block copolymer having a weight ratio of ε-caprolactone to lactide of at least 1/1 shows low burst release.

Table 6 shows that the at least partially acylated tri-block copolymers of the invention can form a gel.

Figure 5:
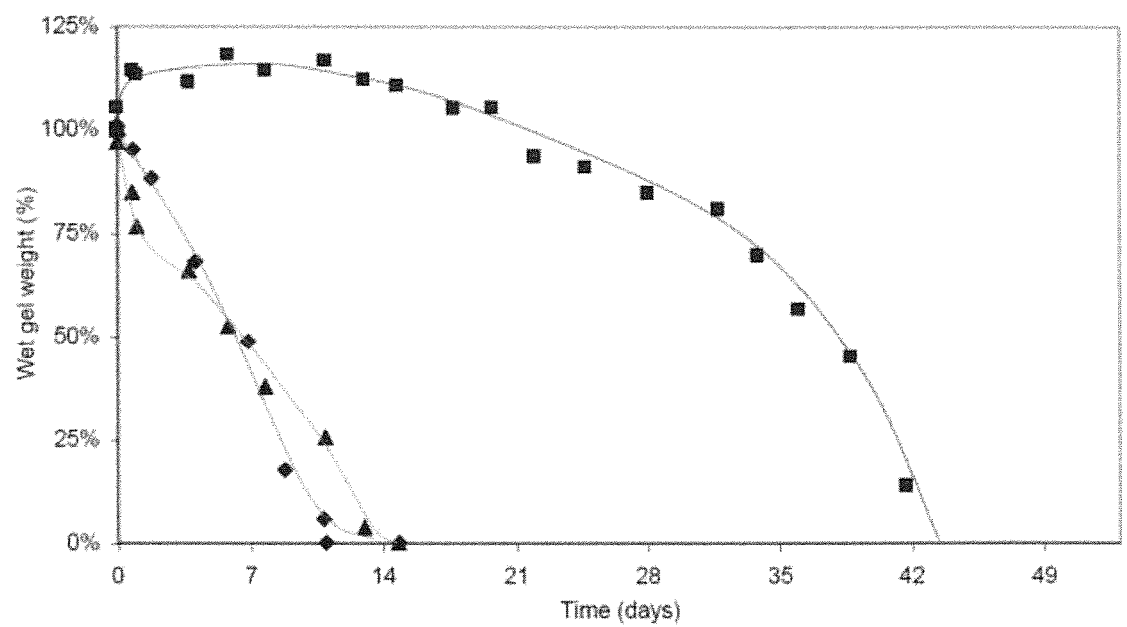
FIG. 5 shows the degradation profile of the relative wet gel as a function of time for formulations of 20 wt % of polymer and 3 wt % of lysozyme. Measurements were made on 4 samples (n=4)

As shown in FIG. 5 and Table 7, the composition having a degree of acylation of the end-groups of at least 75% for example of 100% have a significantly longer degradation time (42 days) than those compositions having a lower degree of acylation.

Figure 6:
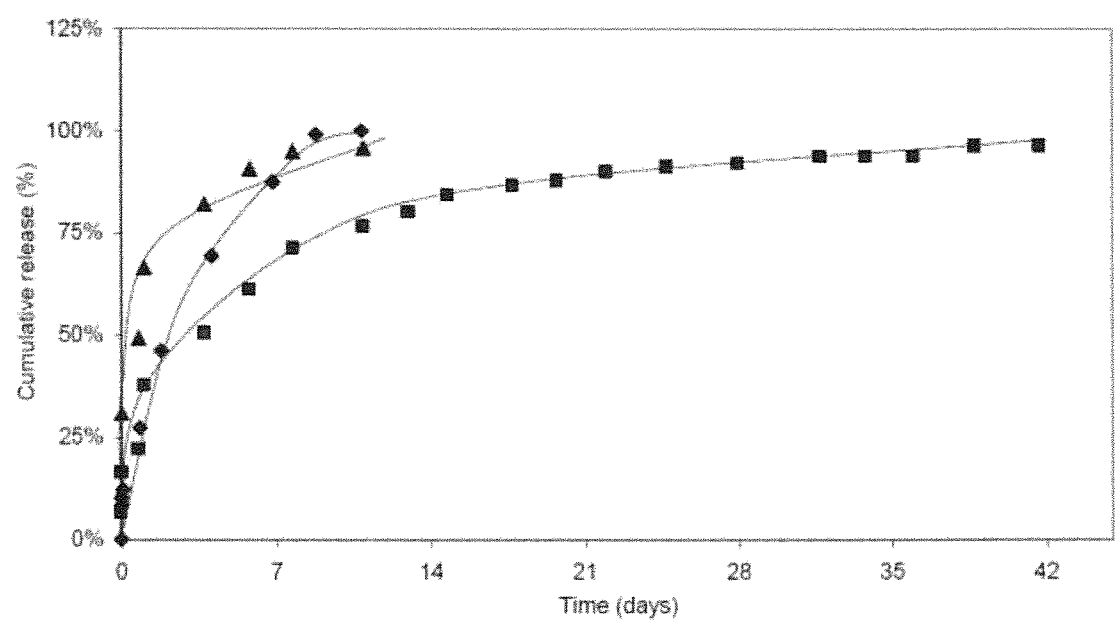
FIG. 6 shows the cumulative release profile of lysozyme as a function of time for formulations of 20 wt % of tri-block copolymer and 3 wt % of lysozyme.

As can be seen from FIG. 6, the compositions comprising a tri-block copolymer that is at least partially acylated (degree of acylation 50%) or fully acylated (degree of acylation 100%) provide gels with a lower burst release, when compared to compositions comprising a tri-block copolymer that is not acylated. This example clearly demonstrates the surprising improvement in terms of release profile of a water soluble protein from a composition according to the invention comprising an at least partially acylated tri-block copolymer e.g. having a degree of acylation of at least 75% in comparison with the composition comprising a tri-block copolymer lacking acylation.

Figure 7:
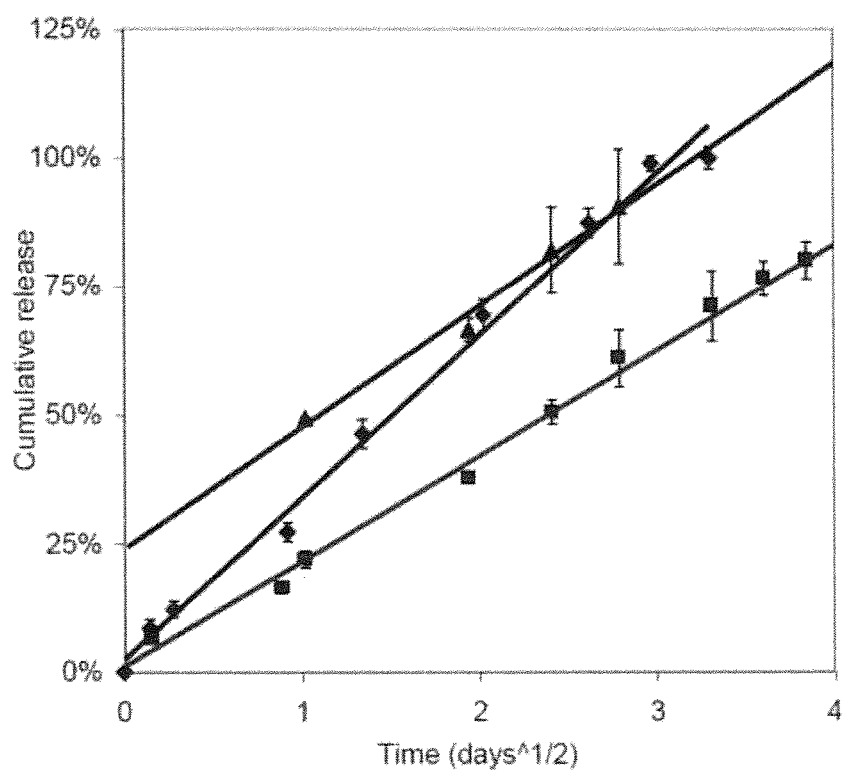
FIG. 7 shows the cumulative release profiles of lysozyme from tri-block copolymer compositions as a function of the square root of time. The formulations comprised 20 wt % of tri-block copolymer and 3 wt % of lysozyme. Lines represent linear fits. The fitted curves correspond to y=mx+c where c is the percentage burst release. Error bars show the standard deviation with n=4.
Figure 8:
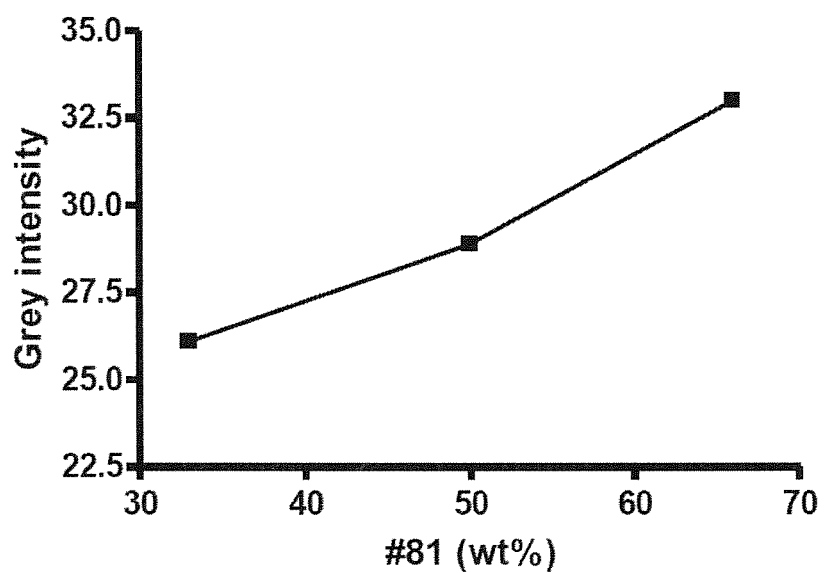
FIG. 8 shows the x-ray intensities as measured by the microCT, for compositions shown in Table 10, example 16, whereby the percentage of iodine bound polymer P(#81) is given on the x-axis. The line is added to guide the eye.
Figure 9:
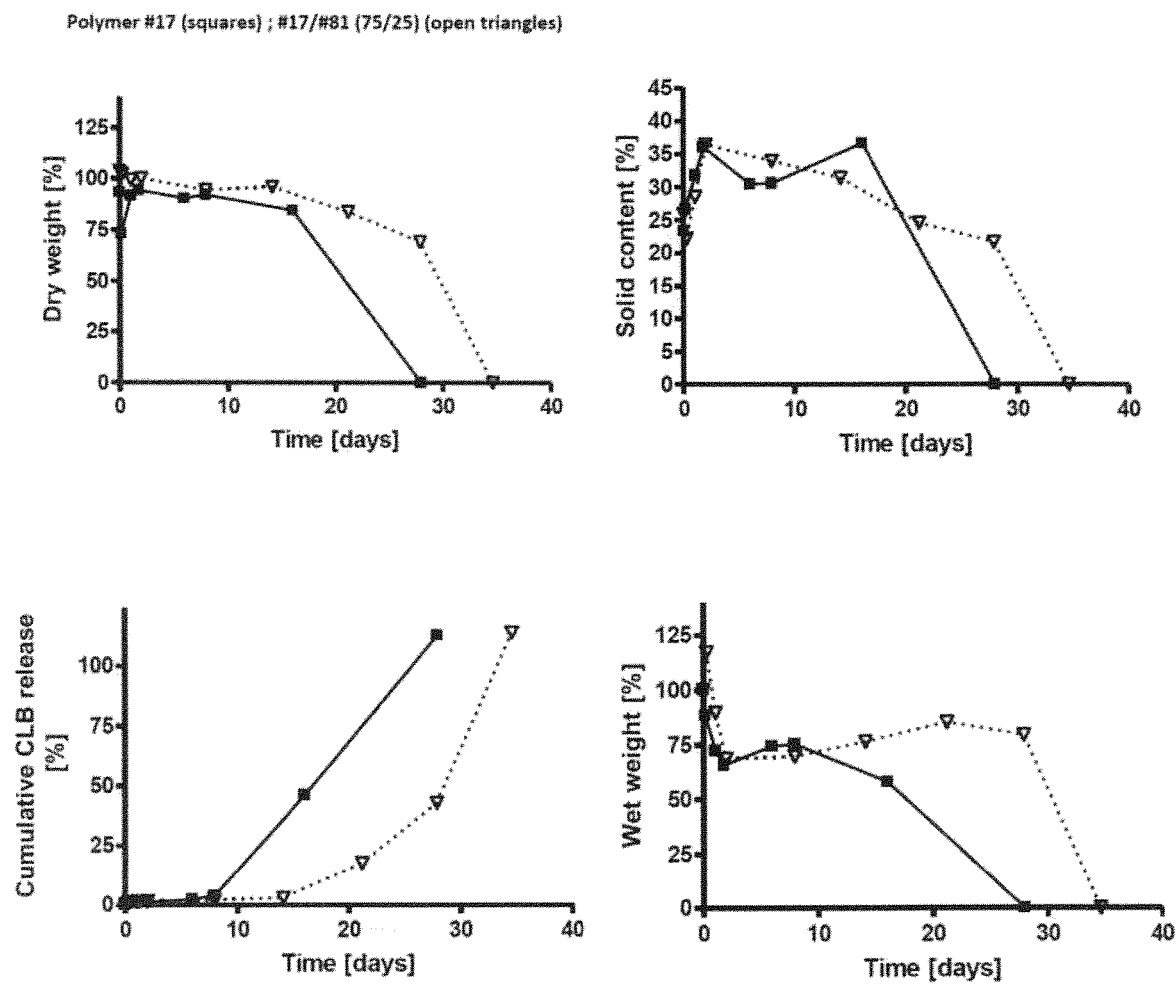
FIG. 9 shows the release profile and gel erosion profiles for example 18. The filled squares indicate composition 18a (OAc-Gell only loaded with Celecoxib) and the empty triangles indicate composition 18b (OAc-Gell/I-Gell®#1-#81). The compositions contained 25 wt % in 50 mM phosphate buffer, pH 7.4, 0.42% NaCl and 0.05% NaN3. The loading of Celecoxib was 1.25 mg/mL.
Figure 10:
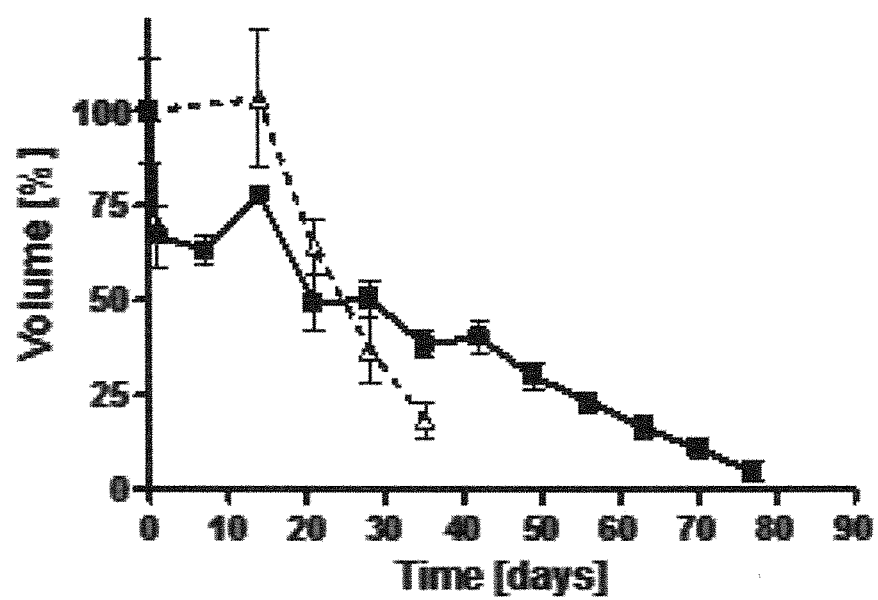
FIG. 10 shows the erosion profile for compositions 19a (dotted line) and 19b (Solid line). Images of the subcutaneous injected I-Gell depots in rats were taken in-vivo using micro-CT on days 0-1-4-8-14-21-28-35-42-49-56-63-70-77 and the volume of the gel was determined using a caliper as done routinely for volume-estimations of subcutaneous tumor lumps.
Figure 11:
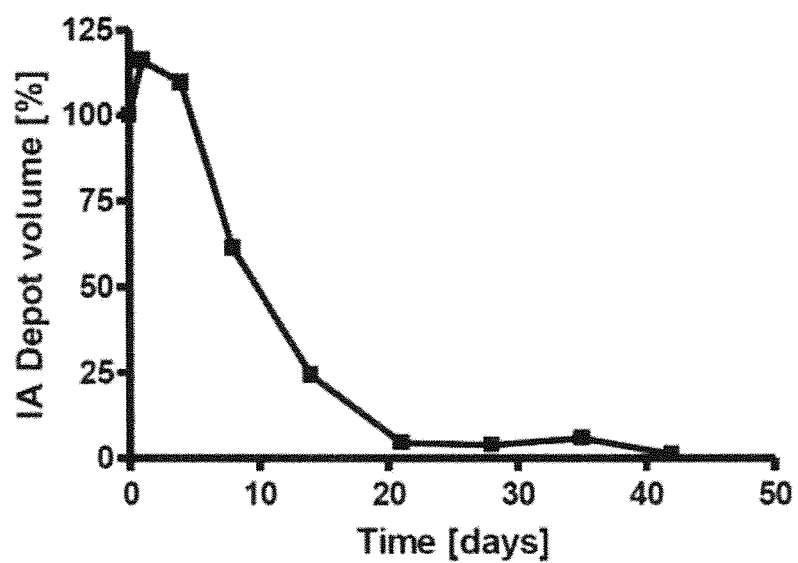
FIG. 11 shows the degradation profile for composition 17b as determined by visualization using microCT.

As can clearly be seen from FIG. 7, compositions comprising at least partially acylated (e.g. degree of acylation 50%) or fully acylated end-groups (e.g. degree of acylation 100% tri-block co polymers) have a burst release of less than 2%, which is surprising and significant improvement for use in controlled release of especially water soluble compounds, for example water soluble proteins. The composition comprising non-acylated caprolactone/lactide showed a burst release of 24% with the same water soluble compounds. which renders this composition useless, and even unsafe, in clinical practise for most protein-based drug therapies.

The conclusion that can be drawn from the mathematical analysis (as shown in FIG. 7) of the release profile is that compositions of the invention comprising tri-block copolymers that are at least partially acylated give low or very low burst release compared to compositions comprising tri-block copolymers that are not acylated.

It is also observed, that when using triblock copolymers in the composition of the invention, wherein the number average molecular weight of the A-block is 1000 Da, we obtain gels at 37° C. that immediately phase separate. When using triblock copolymers in the composition of the invention, wherein the number average molecular weight of the A-block is at least 1250 Da (as exemplified by the number average molecular weight of the A-block of 1500), gels are obtained at 37° C. that do not phase separate. Phase separation results in expulsion of free water/buffer from the interior of the gel-matrix, and shrinkage of the gel-matrix expressed as wet weight. Water-dissolved molecules will also exit the gel in large quantities with the expulsion of water-based solvents, hence leading to fast and high quantity release of the loaded water soluble molecules, which we refer to as burst or burst release. Avoiding early stage phase separation of the formulation is essential to keep water soluble drug-molecules inside the gel until they are released by diffusion and/or by gradual degradation of the gel-matrix.

In conclusion the examples presented herein show that the block ratio of the PEG/PLCA tri-copolymer is important and the ratio needs to be greater than 1.2 but less than 2.8 in order to obtain a non-phase separating gel at 37 C. Furthermore, tri-block copolymers which are at least partially acylated have unexpected properties in a composition of the invention, when compared to compositions comprising unacylated tri-block copolymers. Notably the at least partial covalent modification of hydroxyl end groups of tri-block copolymers is very suitable for the sustained, controlled release of a pharmaceutically active ingredient, for example a water soluble drug, and results hardly in any burst release of water soluble molecules.

Furthermore, a tri-block copolymer loaded with Hexabrix™ can be used for imaging in microCT studies but the contrast agent diffuses out of the tri-block copolymer within 1 day thereby preventing prolonged imaging of the tri-block copolymer. Surprisingly, a composition comprising a tri-block copolymer wherein at least part of the hydroxyl end-groups of the tri-block copolymer are covalently bound to a compound containing radiopaque atoms is suitable for microCT imaging over longer periods of up to time.

It is shown herein that a composition comprising a tri-block copolymer wherein at least part of the hydroxyl end-groups of the tri-block copolymer are covalently bound to a compound containing radiopaque atoms maintains gel forming, gel erosion and controlled release properties whilst at the same time such composition can be visualized using micro CT.

Furthermore it is shown that it is possible to visualize, e.g. using microCT or CT imaging, a blend of a tri-block copolymer wherein the hydroxyl end-groups of the tri-block copolymer are at least partially acylated with an acetyl group or wherein at least part of the hydroxyl end-groups of the tri-block copolymer are covalently bound to a compound containing radiopaque atoms, while maintaining gel forming, gel erosion and controlled release properties are maintained.

What is claimed is:

1. A composition, comprising: a tri-block copolymer according to formula 1

$$B-A-B \tag{1}$$

wherein A stands for a linear poly-(ethylene glycol) block and wherein B stands for a poly(lactide-co-ε-caprolactone) block, wherein a weight ratio of ε-caprolactone to lactide is from 1/1 to 9/1;

wherein hydroxyl end-groups of the tri-block copolymer are at least partially acylated, wherein the degree of acylation is at least 75% and is at most 100%, wherein the acyl group is an acetyl group, propionyl group or a butionyl group, an active ingredient, and a solvent, wherein a block ratio of the tri-block copolymer, which ratio is defined as the ratio between a sum of a number average molecular weight of the B-blocks and a number average molecular weight of the A-block ranges from 1.6 to 2.6, wherein a number average molecular weight (Mn) of the linear poly-(ethylene glycol) block is at least 1250 Da and at most 2000 Da, and wherein concentration of the tri-block copolymer in the composition is at least 15% w/w to at most 50% w/w based on the amount of the solvent and active ingredient present in the composition.

2. A composition, comprising: a tri-block copolymer according to formula (1)

B-A-B   (1)

wherein A stands for a linear poly-(ethylene glycol) block and wherein B stands for a poly(lactide-co-ε-caprolactone) block, wherein at least part of hydroxyl end-groups of the tri-block copolymer are covalently bound to a compound containing radiopaque atoms, wherein a weight ratio of ε-caprolactone to lactide is from 1/1 to 9/1, wherein a block ratio of the tri-block copolymer, which ratio is defined as the ratio between a sum of a number average molecular weight of the B-blocks and a number average molecular weight of the A-block ranges from 1.6 to 2.6, wherein a number average molecular weight (Mn) of the linear poly-(ethylene glycol) block is at least 1250 Da and at most 2000 Da, and wherein hydroxyl end-groups of the tri-block copolymer are at least partially acylated with the compound containing radiopaque atoms, wherein the degree of acylation is at least 75% and is at most 100%, wherein concentration of the tri-block copolymer in the composition is at least 15% w/w to at most 50% w/w based on the amount of the solvent and active ingredient present in the composition.

3. The composition according to claim 2, wherein the composition further comprises an active ingredient and a solvent.

4. The composition according to claim 1, wherein a concentration of the tri-block copolymer in the composition of the invention ranges from 21 to 35% w/w based on the amount of the solvent and the active ingredient present in the composition.

5. The composition according to claim 1, wherein the acyl group is an acetyl group or a propionyl group.

6. The composition according to claim 1, wherein the active ingredient is a pharmaceutically active ingredient chosen from the group of steroids, and non-steroidal anti-inflammatory drugs.

7. The composition according to claim 1, wherein the active ingredient are microparticles, nano-particles, microspheres containing drugs or imaging agents, or liposomes containing siRNA, miRNA, drugs or imaging agents.

8. The composition according to claim 1, wherein the active ingredient has a solubility of at least 20 μg/ml in water measured at 20° C. and at 1 bar pressure.

9. The composition according to claim 1, wherein the solvent is water or an aqueous buffer solution.

10. The composition according to claim 1, wherein the composition has a gel temperature in the range from 25 to 35° C. and a phase separation temperature of at least 42°.

11. The composition according to claim 1, wherein the tri-block copolymer has a gel window between 25° C. and 42° C.

12. The composition according to claim 1, wherein the acyl group is substituted with a radiopaque atom.

13. The composition according to claim 2, wherein the radiopaque atom is iodine.

14. The composition according to claim 1, wherein the composition is a pharmaceutical composition further comprising a pharmaceutically acceptable adjuvant, excipient or carrier.

15. The composition according to claim 1 for use as a medicament.

16. A process for the preparation of a composition according to claim 1 comprising the steps of
synthesizing the tri-block copolymer; and
mixing the tri-block copolymer with the active ingredient and the solvent.

* * * * *